US011021686B2

(12) United States Patent
Vallier et al.

(10) Patent No.: US 11,021,686 B2
(45) Date of Patent: Jun. 1, 2021

(54) IN VITRO PRODUCTION OF CHOLANGIOCYTES

(71) Applicant: CAMBRIDGE ENTERPRISE LIMITED, Cambridge (GB)

(72) Inventors: Ludovic Vallier, Cambridge (GB); Fotios Sampaziotis, Hitchin (GB); Nicholas Hannan, Wollaton (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 267 days.

(21) Appl. No.: 15/738,282

(22) PCT Filed: Jun. 21, 2016

(86) PCT No.: PCT/GB2016/051853
§ 371 (c)(1),
(2) Date: Dec. 20, 2017

(87) PCT Pub. No.: WO2016/207621
PCT Pub. Date: Dec. 29, 2016

(65) Prior Publication Data
US 2018/0187160 A1 Jul. 5, 2018

(30) Foreign Application Priority Data

Jun. 22, 2015 (GB) ..................................... 1510950

(51) Int. Cl.
*C12N 5/071* (2010.01)
*A61K 35/413* (2015.01)
*G01N 33/50* (2006.01)
*A61P 1/16* (2006.01)

(52) U.S. Cl.
CPC .......... *C12N 5/0672* (2013.01); *A61K 35/413* (2013.01); *A61P 1/16* (2018.01); *C12N 5/067* (2013.01); *C12N 5/0676* (2013.01); *C12N 5/0679* (2013.01); *G01N 33/5008* (2013.01); *G01N 33/5044* (2013.01); *G01N 33/5091* (2013.01); *C12N 2501/11* (2013.01); *C12N 2501/115* (2013.01); *C12N 2501/119* (2013.01); *C12N 2501/15* (2013.01); *C12N 2501/155* (2013.01); *C12N 2501/16* (2013.01); *C12N 2501/36* (2013.01); *C12N 2501/385* (2013.01); *C12N 2501/415* (2013.01); *C12N 2501/42* (2013.01); *C12N 2501/999* (2013.01); *C12N 2503/02* (2013.01); *C12N 2506/14* (2013.01); *C12N 2506/22* (2013.01); *C12N 2506/45* (2013.01); *C12N 2513/00* (2013.01); *C12N 2533/90* (2013.01); *G01N 2800/08* (2013.01)

(58) Field of Classification Search
CPC .... C12N 5/0672; C12N 5/067; C12N 5/0676; C12N 2501/11; C12N 2501/115; C12N 2501/155; C12N 2501/16; C12N 2501/385; A61P 1/16
See application file for complete search history.

(56) References Cited

U.S. PATENT DOCUMENTS

2013/0031645 A1* 1/2013 Touboul ............... C12N 5/0672
800/9

FOREIGN PATENT DOCUMENTS

| WO | 2011/053690 A1 | 5/2011 |
| WO | 2014/044646 A1 | 3/2014 |
| WO | 2014/124527 A1 | 8/2014 |
| WO | 2015/052143 A1 | 4/2015 |
| WO | 2015/140257 A1 | 9/2015 |

OTHER PUBLICATIONS

Kamiya et al. "Human pluripotent stem cell-derived cholangiocytes: current status and future applications" (May 2015), Curr Opin Gastroenterol, vol. 31(3): 233-238. (Year: 2015).*
Dianat et al., Generation of functional cholangiocyte-like cells from human pluripotent stem cells and HepaRG cells, Hepatology, Jun. 20, 2014, pp. 700-714, vol. 60, Issue 2, Wiley, Hoboken, NJ. Supporting Materials starting on p. 16.
Tanimizu et al., "Liver Progenitor Cells Develop Cholangiocyte-Type Epithelial Polarity in Three-dimensional Culture-D", Molecular Biology of the Cell, Feb. 21, 2007, pp. 1472-1479, vol. 18, No. 4, The American Society for Cell Biology, Bethesda, MD.
Tanimizu et al., "Hepatic biliary epithelial cells acquire epithelial integrity but lose plasticity to differentiate into hepatocytes in vitro during development", Journal of Cell Science, Sep. 17, 2013, vol. 126, No. 22, The Company of Biologists Ltd., Cambridge, United Kingdom.
Hannan et al., "Generation of Multipotent Foregut Stem Cells from Human Pluripotent Stem Cells". Stem Cell Reports, Oct. 1, 2013, pp. 293-306, vol. 1, No. 4, Elsevier, Amsterdam, Netherlands.
Sampaziotis et al., "Cholangiocytes derived from human induced pluripotent stem cells for disease modeling and drug validation", Nature Biotechnology, Jul. 13, 2015, pp. 845-852, vol. 33, No. 8, Nature Publishing Group, London, United Kingdom.

* cited by examiner

*Primary Examiner* — Teresa E Knight
(74) *Attorney, Agent, or Firm* — Pamela J. Sherwood; Bozicevic, Field & Francis LLP

(57) ABSTRACT

This invention relates to the efficient generation of cholangiocyte progenitor (CP) cells. Foregut stem cells (FSCs) are cultured in a hepatic induction medium comprising bone morphogenetic protein (BMP) and a TGFβ signalling inhibitor to produce a population of hepatoblasts. The hepatoblasts are then cultured in a biliary induction medium comprising fibroblast growth factor (FGF), retinoic acid and a TGFβ ligand to produce a population of cholangiocyte progenitors (CPs). The cholangiocyte progenitors (CPs) may be matured into cholangiocyte-like cells (CLCs) that display functional properties of Common Bile Duct (CBD) cholangiocytes. Methods, kits, cell populations and uses of these cell populations are provided.

17 Claims, 18 Drawing Sheets

IN VITRO PRODUCTION OF CHOLANGIOCYTES

CROSS REFERENCE

This application is a 371 application and claims the benefit of PCT Application No. PCT/GB2016/051853, filed Jun. 21, 2016, which claims benefit of GB Patent Application No. 1510950.7, filed Jun. 22, 2015, which applications are incorporated herein by reference in their entirety.

FEDERALLY SPONSORED RESEARCH AND DEVELOPMENT

The work leading to this invention has received funding from the European Research Council under the European Union's Seventh Framework Programme (FP7/2007-2013) ERC grant agreement number 281335.

FIELD

This invention relates to the in vitro production of cholangiocytes, cholangiocyte progenitors and cholangiocyte-like cells, for example for use drug screening and disease-modelling.

BACKGROUND

Cholangiocytes constitute the main target for a diverse group of bile duct disorders known as cholangiopathies, ranging from inherited (Cystic Fibrosis associated cholangiopathy), developmental (Alagille Syndrome), autoimmune (Primary Biliary Cirrhosis) to drug or toxin induced disease (1). Cholangiopathies carry significant morbidity and mortality, accounting for up to a third of adult and more than 70% of paediatric liver transplantations (2). Despite their impact, poor access to primary tissue, difficulties culturing and maintaining primary cholangiocytes in vitro and physiological limitations of animal models restrict our insight in the pathophysiology of cholangiopathies (3).

Human Induced Pluripotent Stem cells (hIPSCs) present a unique opportunity for overcoming such challenges (4). Indeed, their capacity to proliferate indefinitely in vitro and differentiate into a broad spectrum of cell types renders them ideal for in vitro disease modeling (5). However, the translational potential of hIPSCs for the study of biliary disorders is significantly restricted by challenges in the generation of hIPSC-derived cholangiocytes. Indeed, current protocols demonstrate poor differentiation efficiency (<31%) (6), while global gene expression analyses highlight significant differences between hIPSC-derived cholangiocytes and primary biliary tissue (6). Furthermore, in vitro generated cholangiocytes fail to reproduce key functions of their in vivo counterparts, such as enzymatic (Gamma Glutamyl-Transferase (GGT) and Alkaline Phosphatase (ALP)) activity, response to hormonal stimuli (secretin and somatostatin) and chloride transfer (CFTR function) (6-8). These properties are essential for recapitulating the pathogenesis of cholangiopathies or studying the effects of therapeutic agents. Finally, current systems diverge from the physiological pathways controlling biliary development in vivo (6-8), which restricts their value for developmental studies interrogating the mechanisms of biliary specification and differentiation. As a result, medical and pharmaceutical applications of hIPSC derived cholangiocytes towards disease modelling and drug screening have not yet been possible.

SUMMARY

The present inventors have developed a process for the efficient generation of cholangiocyte progenitors (CPs) and cholangiocyte-like cells (CLCs) that display functional properties of Common Bile Duct (CBD) cholangiocytes.

An aspect of the invention provides a method for producing a population of cholangiocyte progenitors (CPs) comprising:
 (i) culturing a population of foregut stem cells (FSCs) in a hepatic induction medium comprising bone morphogenetic protein (BMP) and a TGFβ signalling inhibitor to produce a population of hepatoblasts, and
 (ii) culturing the hepatoblasts in a biliary induction medium comprising fibroblast growth factor (FGF), retinoic acid and a TGFβ ligand to produce a population of cholangiocyte progenitors (CPs).

Another aspect of the invention provides a method for producing a population of cholangiocyte progenitors (CPs) comprising:
 (i) culturing a population of pluripotent stem cells (PSCs) in an endoderm induction medium comprising a TGFβ ligand, fibroblast growth factor (FGF), bone morphogenetic protein (BMP), a Wnt signalling activator and a PI3K inhibitor to produce a population of definitive endoderm cells (DECs);
 (ii) culturing the DECs in a foregut induction medium comprising a TGFβ ligand to produce a population of foregut stem cells (FSCs),
 (iii) culturing the population of FSCs in a hepatic induction medium comprising bone morphogenetic protein (BMP) and a TGFβ signalling inhibitor to produce a population of hepatoblasts (HBs), and
 (iv) culturing the population of HBs in a biliary induction medium comprising fibroblast growth factor (FGF), retinoic acid and a TGFβ ligand to produce the population of CPs.

The method may further comprise maturing the cholangiocyte progenitors (CPs) into cholangiocyte-like cells (CLCs).

Another aspect of the invention provides a method for producing a population of cholangiocyte-like cells (CLCs) comprising:
 (i) culturing a population of FSCs in a hepatic induction medium comprising bone morphogenetic protein (BMP) and a TGFβ signalling inhibitor to produce a population of hepatoblasts,
 (ii) culturing the hepatoblasts in a biliary induction medium comprising fibroblast growth factor (FGF), retinoic acid and a TGFβ ligand to produce a population of CPs and
 (iii) culturing the CPs in a cholangiocyte maturation medium comprising epidermal growth factor to produce the population of CLCs.

The CLCs in the population may form one or more organoids in the cholangiocyte maturation medium.

Preferably, the CPs are cultured in three-dimensional culture in the cholangiocyte maturation medium.

Another aspect of the invention provides a population of CPs or CLCs produced by a method described herein.

CPs or CLCs produced by a method described herein may display a normal phenotype or a phenotype comprising one or more pathologies, characteristics or features of a biliary disorder.

Another aspect of the invention provides a population of CPs or CLCs produced by a method described herein for use in the treatment of a biliary disorder.

Another aspect of the invention provides a method of treating a patient with a biliary disorder comprising administering a population of isolated CPs or CLCs produced by a method described herein to an individual in need thereof.

Another aspect of the invention provides a method of screening a compound comprising;
contacting a population of CPs or CLCs produced by a method described herein with a test compound, and;
determining the effect of the test compound on said CPs or CLCs and/or the effect of said CPs or CLCs on the test compound.

Another aspect of the invention provides a method of testing an individual for a biliary disorder comprising;
producing a population of iPSCs from a sample of cells obtained from the individual, producing a population of isolated CPs or CLCs from the iPSCs using a method of an aspect of the invention set out above; and
determining the phenotype of the isolated CPs or CLCs.

The presence of isolated CPs or CLCs with a biliary disorder associated phenotype may be indicative that the individual has a biliary disorder.

Another aspect of the invention provides a kit for production of CPs or CLCs comprising;
a hepatic induction medium comprising bone morphogenetic protein (BMP) and a TGFβ signalling inhibitor,
a biliary induction medium comprising fibroblast growth factor (FGF), retinoic acid and a TGFβ ligand, and optionally
a cholangiocyte maturation medium comprising epidermal growth factor.

Another aspect of the invention provides the use of a set of culture media for the production of CPs or CLCs,
wherein the set of culture media comprises
a hepatic induction medium comprising bone morphogenetic protein (BMP) and a TGFβ signalling inhibitor,
a biliary induction medium comprising fibroblast growth factor (FGF), retinoic acid and a TGFβ ligand, and optionally
a cholangiocyte maturation medium comprising epidermal growth factor.

DETAILED DESCRIPTION

Figure 1:
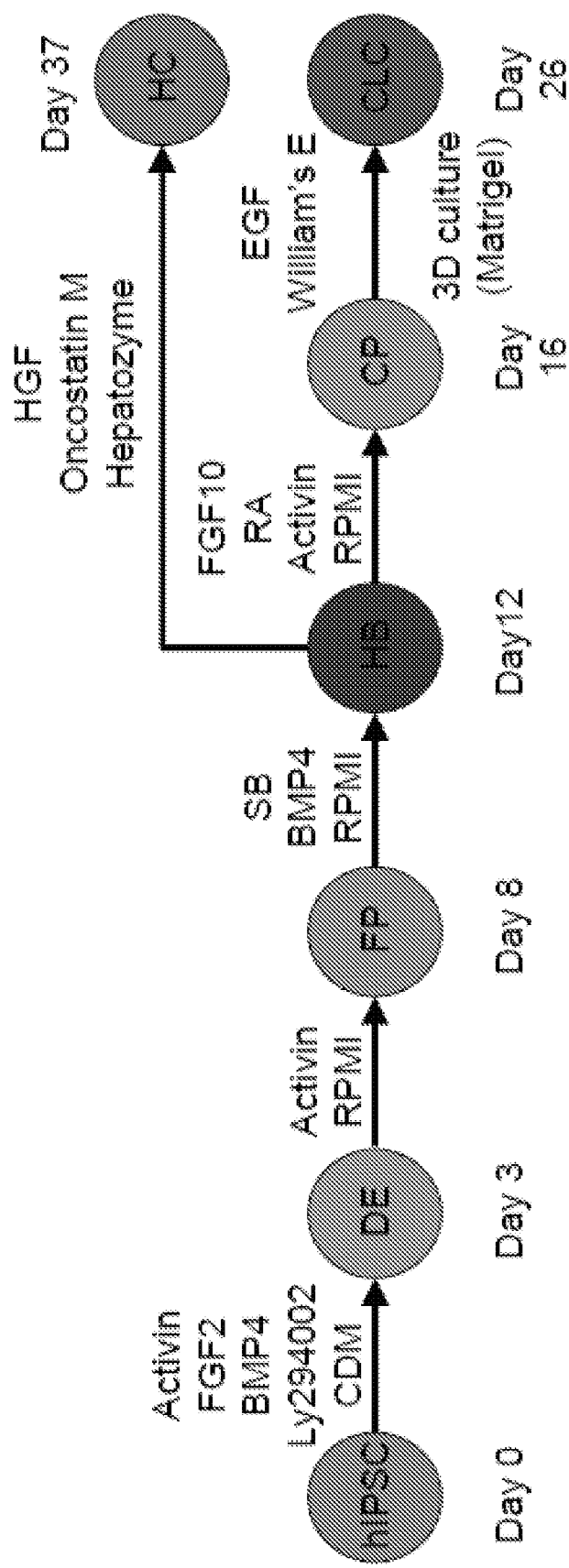
FIG. 1 shows an overview of the protocol used to differentiate hIPSCs to cholangiocyte like cells (CLCs). DE: Definitive endoderm, FP: Foregut progenitors, HB: Hepatoblasts, HC: CPs or CLCs SB: SB431542 RA: Retinoic acid.

This invention relates to the in vitro production of cholangiocyte progenitors (CPs) from foregut stem cells (FSCs).

A population of FSCs may be obtained from a convenient source or produced in vitro from a population of PSCs. The FSCs are differentiated into hepatoblasts by culture in a hepatic induction medium comprising bone morphogenetic protein (BMP) and a TGFβ signalling inhibitor. The resultant hepatoblasts are then differentiated into CPs by culture in a biliary induction medium comprising fibroblast growth factor (FGF), retinoic acid and a TGFβ ligand. The resultant CPs may be matured into cholangiocyte-like cells (CLCs).

Differentiation of the cell population in each step is induced by culturing the cells in a culture medium supplemented with a set of differentiation factors. The set of differentiation factors that is listed for each culture medium is preferably exhaustive and medium may be devoid of other differentiation factors.

Differentiation factors are factors which modulate, for example promote or inhibit, a signalling pathway which mediates differentiation in a mammalian cell. Differentiation factors may include growth factors, cytokines and inhibitors which modulate one or more of the Activin/Nodal, FGF, Wnt or BMP signalling pathways. Examples of differentiation factors include FGFs, BMPs, retinoic acid, TGFβ ligands, GDFs, LIF, IL, GSK-3 inhibitors and phosphatidylinositol 3-kinase (PI3K) inhibitors.

Differentiation factors which are used in one or more of the media described herein include TGFβ ligands, fibroblast growth factor (FGF), bone morphogenetic protein (BMP), PI3K inhibitors, TGFβ signalling inhibitors, Wnt signalling activators and retinoic acid. A differentiation factor may be present in a medium described herein in an amount that is effective to modulate a signalling pathway in cells cultured in the medium.

The extent of differentiation of the cell population during each step may be determined by monitoring and/or detecting the expression of one or more cell markers in the population of differentiating cells. For example, an increase in the expression of markers characteristic of the more differentiated cell type or a decrease in the expression of markers characteristic of the less differentiated cell type may be determined. The expression of cell markers may be determined by any suitable technique, including immunocytochemistry, immunofluorescence, RT-PCR, immunoblotting, fluorescence activated cell sorting (FACS), and enzymatic analysis.

After each step, the population of partially differentiated cells which is produced by that step may be free or substantially free from other cell types. For example, the population may contain 60% or more, 70% or more, 80% or more or 90% or more partially differentiated cells, following culture in the medium. Preferably, the population of cells is sufficiently free of other cell types that no purification is required. If required, the population of partially differentiated cells may be purified by any convenient technique, such as FACS.

A population of partially differentiated cells that is produced by a step in the methods described herein may be cultured, maintained or expanded before the next differentiation step. Partially differentiated cells may be expanded by any convenient technique.

Cells may be cultured in a monolayer, in the absence of feeder cells, on a substrate coated with extracellular matrix protein, such as fibronectin, laminin or collagen, except where otherwise stated. For example, in some embodiments, cells may be embedded in a scaffold matrix and cultured under 3-dimensional culture conditions for cholangiocyte maturation. Suitable techniques for cell culture are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430) Basic Cell Culture Protocols' by J. Pollard and J. M. Walker (1997), 'Mammalian Cell Culture: Essential Techniques' by A. Doyle and J. B. Griffiths (1997), 'Human Embryonic Stem Cells' by A. Chiu and M. Rao (2003), Stem Cells: From Bench to Bedside' by A. Bongso (2005), Peterson & Loring (2012) Human Stem Cell Manual: A Laboratory Guide Academic Press and 'Human Embryonic Stem Cell Protocols' by K. Turksen (2006). Media and ingredients thereof may be obtained from commercial sources (e.g. Gibco, Roche, Sigma, Europa bioproducts, R&D Systems). Standard mammalian cell culture conditions may be employed for the above culture steps, for example 37° C., 21% Oxygen, 5% Carbon Dioxide. Media is preferably changed every two days and cells allowed to settle by gravity.

In the methods described herein, populations of CPs and CLCs are generated from foregut stem cells (FSCs). FSCs are self-renewing cells that resemble the multipotent cells of the anterior primitive gut tube in their capacity to differentiate into endoderm cells of pancreatic, hepatic and pulmonary lineages.

In some preferred embodiments, the FSCs are produced in vitro from pluripotent stem cells (PSCs). Suitable methods are known in the art (see WO2015052143; Hannan et al *Stem Cell Reports,* 1:293-306 (2013)).

Pluripotent stem cells (PSCs) are capable of self-renewal in vitro and exhibit an undifferentiated phenotype and are potentially capable of differentiating into any foetal or adult cell type of any of the three germ layers (endoderm, mesoderm and endoderm). A pluripotent stem cell is distinct from a totipotent stem cell and cannot give rise to extraembryonic cell lineages. The population of PSCs may be clonal i.e. genetically identical cells descended from a single common ancestor cell.

PSCs may express one or more of the following pluripotency associated markers: Oct4, Sox2, Alkaline Phosphatase, POU5f1, SSEA-3, Nanog, SSEA-4, Tra-1-60, KLF-4 and c-myc, preferably one or more of POU5f1, NANOG and SOX2. A PSC may lack markers associated with specific differentiative fates, such as Bra, Sox17, FoxA2, αFP, Sox1, NCAM, GATA6, GATA4, Hand1 and CDX2. In particular, a PSC may lack markers associated with endodermal fates.

Preferably, the PSCs are human PSCs.

PSCs may include embryonic stem cells (ESCs) and non-embryonic stem cells, for example foetal stem cells, adult stem cells, amniotic stem cells, cord stem cells and induced pluripotent stem cells (iPSCs). In some embodiments, the PSCs are not human embryonic stem cells. In some embodiments, the PSCs are not human embryonic cells.

Suitable techniques for generating PSCs are well-known in the art.

Preferably, the PSCs are iPSCs, more preferably human IPSCs (hiPSCs).

iPSCs are pluripotent cells which are derived from non-pluripotent, fully differentiated ancestor or antecedent cells. Suitable ancestor cells include somatic cells, such as adult fibroblasts and peripheral blood cells. Ancestor cells are typically reprogrammed by the introduction of pluripotency genes or proteins, such as Oct4, Sox2 and Sox1 into the cell. The genes or proteins may be introduced into the differentiated cells by any suitable technique, including plasmid or more preferably, viral transfection or direct protein delivery. Other genes, for example Kif genes, such as Kif-1, -2, -4 and -5; Myc genes such as C-myc, L-myc and N-myc; nanog; and Lin28 may also be introduced into the cell to increase induction efficiency. Following introduction of the pluripotency genes or proteins, the ancestor cells may be cultured. Cells expressing pluripotency markers may be isolated and/or purified to produce a population of iPSCs. Techniques for the production of iPSCs are well-known in the art (Yamanaka et al Nature 2007; 448:313-7; Yamanaka 6 2007 Jun. 7; 1(1):39-49; Kim et al Nature. 2008 Jul. 31; 454 (7204):646-50; Takahashi Cell. 2007 Nov. 30; 131(5):861-72. Park et al Nature. 2008 Jan. 10; 451(7175):141-6; Kimet et al Cell Stem Cell. 2009 Jun. 5; 4(6):472-6; Vallier, L., et al. Stem Cells, 2009. 9999(999A): p. N/A).

iPSCs may be derived from somatic cells, such as fibroblasts, which have a normal (i.e. non-disease associated) genotype, for example cells obtained from an individual with a normal genetic background e.g. an individual without a genetic disorder. The iPSCs may be used to produce FSCs with a normal (i.e. non-disease associated) genotype. These FSCs may be further differentiated into CPs and CLCs as described herein, for example for use in therapy, modelling, screening or other applications.

In some embodiments, iPSCs may be derived from somatic cells or other antecedent cells obtained from an individual with a distinct genetic background. For example, iPSCs may be produced from cells from an individual having a disease condition, an individual having a high risk of a disease condition and/or an individual with a low risk of a disease condition. Disease conditions may include biliary disorders e.g. a cholangiopathy or other disorder associated with the bile duct epithelium. iPSCs produced from cells obtained from an individual with a distinct genetic background may be used to produce FSCs which may be further differentiated into CPs and CLCs which possess the genetic background. These CPs and CLCs may be useful in studying the mechanisms of disease conditions, such as biliary disorders, and in identifying therapeutic targets.

Conventional techniques may be employed for the culture and maintenance of PSCs (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)). PSCs for use in the present methods may be grown in defined conditions or on feeder cells. For example, PSCs may be conventionally cultured in a culture dish on a layer of feeder cells, such as irradiated mouse embryonic fibroblasts (MEF), at an appropriate density (e.g. $10^5$ to $10^6$ cells/60 mm dish), or on an appropriate substrate with feeder conditioned or defined medium. Pluripotent cells for use in the present methods may be passaged by enzymatic or mechanical means.

In preferred embodiments, PSCs for use in the present methods may be cultured in chemically defined medium (CDM). A chemically defined medium (CDM) is a nutritive solution for culturing cells which contains only specified components, preferably components of known chemical structure. A CDM is devoid of undefined components or constituents which include undefined components, such as feeder cells, stromal cells, serum, serum albumin and complex extracellular matrices, such as Matrigel™. In some embodiments, the chemically defined medium is humanised. A humanised chemically defined medium is devoid of components or supplements derived or isolated from non-human animals, such as Foetal Bovine Serum (FBS) and Bovine Serum Albumin (BSA), and mouse feeder cells. Conditioned medium includes undefined components from cultured cells and is not chemically defined.

A CDM may comprise a chemically defined basal medium supplemented with a serum-free media supplement and/or one or more additional components, for example transferrin, 1-thioglycerol, defined lipids, L-glutamine or substitutes, such as GlutaMAX-1™, nicotinamide, dexamethasone, selenium, pyruvate, buffers, such as HEPES, sodium bicarbonate, glucose and antibiotics such as penicillin and streptomycin and optionally polyvinyl alcohol; polyvinyl alcohol and insulin; serum albumin; or serum albumin and insulin.

Suitable chemically defined basal medium, such as Advanced Dulbecco's modified eagle medium (DMEM) (Price et al Focus (2003) 25 3-6), Iscove's Modified Dulbecco's medium (IMDM), William's E medium and RPMI-1640 (Moore, G. E. and Woods L. K., (1976) Tissue Culture Association Manual. 3, 503-508; see Table 3) are known in the art and available from commercial sources (e.g. Sigma-Aldrich MI USA; Life Technologies USA). Other suitable chemically defined basal medium are known in the art and available from commercial sources (e.g. Sigma-Aldrich MI USA; Life Technologies USA).

Suitable serum-free media supplements include B27 (Brewer et al Brain Res (1989) 494 65-74; Brewer et al J. Neurosci Res 35 567-576 (1993); Brewer et al Focus 16 1 6-9; Brewer et al (1995) J. Neurosci. Res. 42:674-683; Roth et al J Trace Elem Med Biol (2010) 24 130-137) and NS21 (Chen et al J. Neurosci Meths (2008) 171 239-247). Serum-free media supplements, such as B27 and N21, are well-known in the art and widely available commercially (e.g. Invitrogen; Sigma Aldrich Inc).

Suitable chemically defined media include CDM-PVA (Johansson and Wiles (1995) Mol Cell Biol 15, 141-151), which comprises a basal medium supplemented with polyvinyl alcohol, insulin, transferrin and defined lipids. For example, a CDM-PVA medium may consist of: 50% Iscove's Modified Dulbecco's Medium (IMDM) plus 50% Ham's F12 with GlutaMAX-1™ or 50% F12 NUT-MIX (Gibco, supplemented with 1% chemically defined lipid concentrate, 4501M 1-thiolglycerol, 15 µg/ml transferrin, 1 mg/ml polyvinyl alcohol, 7 µg/ml Insulin. Other suitable chemically defined nutrient media include hESC maintenance medium (CDMA) which is identical to the CDM-PVA described above with the replacement of PVA with 5 mg/ml BSA; and RPMI basal medium supplemented with B27 and Activin (for example at least 50 ng/ml). CDM-PVA media are described in Vallier et al 2009 PLoS ONE 4: e6082. doi: 10.1371; Vallier et al 2009 Stem Cells 27: 2655-2666, Touboul 2010 51: 1754-1765. Teo et al 2011 Genes & Dev. (2011) 25: 238-250 and Peterson & Loring Human Stem Cell Manual: A Laboratory Guide (2012) Academic Press.

PSCs may be differentiated into FSCs in a two-step process comprising differentiation of the PSCs into definitive endoderm cells (DECs), followed by differentiation of the DECs into FSCs. Suitable methods are described in WO2015052143; Hannan et al Stem Cell Reports, 1:293-306 (2013). For example, the PSCs may be differentiated into DECs by culturing in an endoderm induction medium comprising a TGFβ ligand, fibroblast growth factor (FGF), a Wnt signalling activator, bone morphogenetic protein (BMP) and a PI3K inhibitor. The resultant DECs may be differentiated into FSCs by culturing in a foregut induction medium comprising a TGFβ ligand.

A method for producing a population of CPs may comprise:
(i)) culturing a population of PSCs in a endoderm induction medium comprising a TGFβ ligand, fibroblast growth factor (FGF), a Wnt signalling activator, bone morphogenetic protein (BMP) and a PI3K inhibitor to produce a population of definitive endoderm cells (DECs),
(ii) culturing the DECs in a foregut induction medium comprising a TGFβ ligand to produce a population of FSCs,
(iii) culturing the FSCs in a hepatic induction medium comprising bone morphogenetic protein (BMP) and a TGFβ signalling inhibitor to produce a population of hepatoblasts (HBs), and.
(iv) culturing the HBs in a biliary induction medium comprising fibroblast growth factor (FGF), retinoic acid and a TGFβ ligand to produce a population of CPs.

In some embodiments, the method may further comprised (v) culturing the population of CPs in a cholangiocyte maturation medium comprising epidermal growth factor to produce a mature population of CLCs.

In preferred embodiments, the endoderm induction medium is a chemically defined medium comprising a TGFβ ligand, a fibroblast growth factor (FGF), a Wnt signalling activator, a bone morphogenetic protein (BMP) and a PI3K inhibitor.

TGFβ ligands are peptides of the TGFβ superfamily which stimulate SMAD2 and SMAD3 mediated intracellular signalling pathways in mammalian cells. Members of the TGFβ superfamily possess a characteristic structure and are well-known in the art. Suitable TGFβ ligands include Activin, TGFβ, Nodal, or GDF3. Preferably, the TGFβ ligand is activin.

Activin (Activin A: NCBI GeneID: 3624 nucleic acid reference sequence NM_002192.2 GI: 62953137, amino acid reference sequence NP_002183.1 GI: 4504699) is a dimeric polypeptide which exerts a range of cellular effects via stimulation of the Activin/Nodal pathway (Vallier et al., Cell Science 118:4495-4509 (2005)). Activin is readily available from commercial sources (e.g. Stemgent Inc. MA USA). Conveniently, the concentration of Activin in a medium described herein may be from 10 to 1000 ng/ml, preferably about 100 ng/ml.

TGFβ (NCBI GeneID: 7040 nucleic acid reference sequence NM_000660.4 GI: 260655621, amino acid reference sequence NP_000651.3 GI: 63025222) is a homodimeric polypeptide which regulates proliferation and differentiation (Watabe, T. et al (2009). Cell Res. 19:103-115). Recombinant human TGFβ is readily available from commercial sources (e.g. Stemgent Inc. MA USA). Conveniently, the concentration of TGFβ in the medium may be from 10 to 1000 ng/ml, preferably about 100 ng/ml.

GDF3 (NCBI Gene ID 9573 nucleic acid sequence reference NM_020634.1 GI:10190669, amino acid sequence reference NP_065685.1 GI:10190670) is a member of TGFβ superfamily which is characterized by a polybasic proteolytic processing site that is cleaved to produce a mature GDF3 protein containing seven conserved cysteine residues. Conveniently, the concentration of GDF3 in the medium may be from 10 to 1000 ng/ml, preferably about 100 ng/ml.

Nodal (NCBI GeneID 4838 nucleic acid sequence reference NM_018055.4 GI:222352097, amino acid sequence reference NP_060525.3 GI:222352098) is a member of the TGFβ superfamily which regulates differentiation (Hamada et al Nat. Rev. Genet. 3 (2): 103-13). Nodal is readily available from commercial sources (e.g. Abcam Ltd, UK). Conveniently, the concentration of Nodal in the medium may be from 10 to 1000 ng/ml, preferably about 100 ng/ml.

Fibroblast growth factor (FGF) is a protein factor which stimulates cellular growth, proliferation and cellular differentiation by binding to a fibroblast growth factor receptor (FGFR). Suitable fibroblast growth factors include any member of the FGF family, for example any one of FGF1 to FGF14 and FGF15 to FGF23.

Preferably, the FGF is FGF2 (also known as bFGF, NCBI GeneID: 2247, nucleic acid sequence NM_002006.3 GI: 41352694, amino acid sequence NP_001997.4 GI: 41352695); FGF7 (also known as keratinocyte growth factor (or KGF), NCBI GeneID: 2247, nucleic acid sequence NM_002006.3 GI: 41352694, amino acid sequence NP_001997.4 GI: 41352695); or FGF10 (NCBI GeneID: 2247, nucleic acid sequence NM_002006.3 GI: 41352694, amino acid sequence NP_001997.4 GI: 41352695). Most preferably, the fibroblast growth factor is FGF10 or FGF2.

Fibroblast growth factors, such as FGF2, FGF7 and FGF10, may be produced using routine recombinant techniques or obtained from commercial suppliers (e.g. R&D Systems, Minneapolis, Minn.; Stemgent Inc, USA).

In some embodiments, FGF may be replaced by epidermal growth factor (EGF; NCBI GeneID: 1950, nucleic acid sequence NM_001178130.1 GI: 296011012; amino acid sequence NP_001171601.1 GI: 296011013). Epidermal growth factor is a protein factor which stimulates cellular growth, proliferation and cellular differentiation by binding to an epidermal growth factor receptor (EGFR). EGF may be produced using routine recombinant techniques or obtained from commercial suppliers (e.g. R&D Systems, Minneapolis, Minn.; Stemgent Inc, USA).

Bone Morphogenic Proteins (BMPs) bind to Bone Morphogenic Protein Receptors (BMPRs) and stimulate intracellular signalling through pathways mediated by SMAD1, SMAD5 and SMAD9. Suitable Bone Morphogenic Proteins include any member of the BMP family, for example BMP2, BMP3, BMP4, BMP5, BMP6 or BMP7. Preferably the second TGFβ ligand is BMP2 (NCBI GeneID: 650, nucleic acid sequence NM_001200.2 GI: 80861484; amino acid sequence NP_001191.1 GI: 4557369) or BMP4 (NCBI GeneID: 652, nucleic acid sequence NM_001202.3 GI: 157276592; amino acid sequence NP_001193.2 GI: 157276593). Suitable BMPs include BMP4. Conveniently, the concentration of a Bone Morphogenic Protein, such as BMP2 or BMP4 in a medium described herein may be from 1 to 500 ng/ml, preferably about 10 ng/ml.

BMPs may be produced using routine recombinant techniques or obtained from commercial suppliers (e.g. R&D, Minneapolis, USA, Stemgent Inc, USA).

PI3K inhibitors inhibit the activity of phosphatidylinositol 3-kinases, such as phosphatidylinositol-4, 5-bisphosphate 3-kinase (EC2.7.1.153). Suitable PI3K inhibitors include wortmannin; LY301497 (17-b-hydroxywortmannin); LY294002 (2-morpholin-4-yl-8-phenylchromen-4-one: Maclean et al (2007) Stem Cells 25 29-38); CLB1309 (KN309: (±)-2-({1-[7-methyl-2-(morpholin-4-yl)-4-oxopyrido[1,2-a]pyrimidin-9-yl]ethyl}amino)benzoic acid); PX-866 ((1E,4S,4aR,5R,6aS,9aR)-5-(Acetyloxy)-1-[(di-2-propen-1-ylamino)methylene]-4,4a,5,6,6a,8,9,9a-octahydro-11-hydroxy-4-(methoxymethyl)-4a,6a-dimethylcyclopenta [5,6]naphtho[1,2-c]pyran-2,7,10(1H)-trione); IC87114 (quinolone pyrrolopyrimidine); GDC-0941 (2-(1H-Indazol-4-yl)-6-[[4-(methylsulfonyl)-1-piperazinyl] methyl]-4-(4-morpholinyl)-thieno[3,2-d]pyrimidine); TGX-221 (7-methyl-2-(4-morpholinyl)-9-[1-(phenylamino) ethyl]-4H-pyrido[1,2-a]pyrimidin-4-one), quercetin; BEZ235; XL147; XI765; PX-866; ZSTK474 (2-(2-difluoromethylbenzimidazol-1-yl)4,6-dimorpholino-1,3,5-triazine); and SF1126 (2-[2-methoxyethylamino]-8-phenyl-4H-1-benzopyran-4-one). Other PI3K inhibitors are available in the art. In some preferred embodiments, the PI3K inhibitor is LY294002. Conveniently, a medium may contain 1 to 100 µM PI3K inhibitor, such as LY294002, preferably about 10 µM.

Suitable PI3K inhibitors may be obtained from commercial suppliers (e.g. Calbiochem CA USA).

TGFβ signalling inhibitors are antagonists of activin/TGFβ which block SMAD2 and SMAD3 mediated intracellular signalling pathways in mammalian cells. A number of TGFβ signalling inhibitors are known, including SB431542 (4-(5-Benzol[1,3]dioxol-5-yl-4-pyridin-2-yl-1H-imidazol-2-yl)-benzamide hydrate; Sigma, Tocris Bioscience, Bristol UK), SB-505124 (2-(5-benzo[1,3]dioxol-5-yl-2-tert-butyl-3H-imidazol-4-yl)-6-methylpyridine hydrochloride) and a soluble protein factor, such as lefty (e.g. human lefty 2: NP_003231.2 GI:27436881), cerberus (e.g. human Cerberus 1: NP_005445.1 GI:4885135) or follistatin (e.g. human foistatin: NP_006341.1 GI:5453652). Conveniently, the concentration of TGFβ signalling inhibitor in the medium may be from 1 to 100 µM, preferably about 10 µM.

TGFβ signalling inhibitors are available from commercial suppliers (e.g. Sigma Aldrich, USA; Stemgent Inc, USA).

Retinoic acid (2E,4E,6E,8E)-3,7-dimethyl-9-(2,6,6-trimethylcyclohexen-1-yl)nona-2,4,6,8-tetraenoic acid) is a metabolite of vitamin A that modulates transcription through binding to the retinoic acid receptor (RAR) and modulates differentiation in a range of cell types. Preferably all-trans retinoic acid is employed in media described herein. Conveniently, the concentration of retinoic acid in a medium may be 1 to 10 µM of preferably about 2 µM.

Retinoic acid is available from commercial suppliers (e.g. Sigma Aldrich, USA; Stemgent Inc, USA).

Wnt signalling activators stimulate canonical Wnt intracellular signalling pathways in mammalian cells (Logan and Nusse (2004), Annu. Rev. Cell Dev. Biol. 20, 781-810 and Wodarz and Nusse (1998), Annu. Rev. Cell Dev. Biol. 14, 59-80). Suitable Wnt signalling activators include Wnt ligands, glycogen synthase kinase 3β (GSK3β) inhibitors: β-catenin and activators of β-catenin.

Wnt signalling activators may include (hetero)arylpyrimidines (Gilbert et al Bioorg Med Chem Lett. 2010 Jan. 1; 20(1):366-70), WAY-316606 (Bodine et al Bone. 2009 June; 44(6):1063-8), IQ1 (Miyabayashi et al PNAS USA 2007 104(13) 5668-5673), QS11 (Zhang et al (2007) PNAS USA 104(18) 7444-7448), and 2-amino-4-[3,4-(methylenedioxy) benzyl-amino]-6-(3-methoxyphenyl)pyrimidine (Liu et al Angew Chem Int Ed Engl. 2005 Mar. 18; 44(13):1987-90)

In some preferred embodiments, the Wnt signalling activator is a GSK3β inhibitor. GSK3β inhibitors inhibit the activity of glycogen synthase kinase 3β (Gene ID 2932: EC2.7.11.26). Suitable inhibitors include CHIR99021 (6-((2-((4-(2,4-Dichlorophenyl)-5-(4-methyl-1H-imidazol-2-yl)pyrimidin-2-yl)amino)ethyl)amino)nicotinonitrile; Ring D. B. et al., Diabetes, 52:588-595 (2003)) alsterpaullone, kenpaullone, BIO(6-bromoindirubin-3'-oxime (Sato et al Nat Med. 2004 January; 10(1):55-63), SB216763 (3-(2,4-dichlorophenyl)-4-(1-methyl-1H-indol-3-yl)-1H-pyrrole-2, 5-dione), and SB415286 (3-[(3-chloro-4-hydroxyphenyl) amino]-4-(2-nitrophenyl)-1H-pyrrole-2,5-dione; Coghlan et al Chem Biol. 2000 October; 7(10):793-803).

In some preferred embodiments, the GSK3β inhibitor is CHIR99021.

Suitable glycogen synthase kinase 3β inhibitors may be obtained from commercial suppliers (e.g. Stemgent Inc. MA USA; Cayman Chemical Co. MI USA). For example, the endoderm induction medium may contain 0.3 to 30 µM of a GSK3β inhibitor, such as CHIR99021, preferably about 3 µM.

The endoderm induction medium may be devoid of differentiation factors other than the TGFβ ligand, fibroblast growth factor (FGF), Wnt signalling activator, bone morphogenetic protein (BMP) and PI3K inhibitor.

For example, the endoderm induction medium may consist of a chemically defined nutrient medium supplemented with an effective amount of a TGFβ ligand, fibroblast growth factor (FGF), Wnt signalling activator, bone morphogenetic protein (BMP) and a PI3K inhibitor. The TGFβ ligand may be activin, the Wnt signalling activator may be CHIR99021 and/or the PI3K inhibitor may be LY294002. The endoderm induction medium may consist of a chemically defined nutrient medium, such as CDM-PVA, supplemented with activin, fibroblast growth factor (FGF). CHIR99021, bone morphogenetic protein (BMP) and LY294002.

The chemically defined nutrient medium may comprise a chemically defined basal medium. Suitable chemically defined basal media are described above and include Iscove's Modified Dulbecco's Medium (IMDM), Ham's F12, Advanced Dulbecco's modified eagle medium (DMEM) (Price et al Focus (2003), 25 3-6), Williams E (Williams, G. M. et al Exp. Cell Research, 89, 139-142 (1974)), and RPMI-1640 (Moore, G. E. and Woods L. K., (1976) Tissue Culture Association Manual. 3, 503-508).

The basal medium may be supplemented by serum-tree culture medium supplements and/or additional components in the endoderm induction medium. Suitable supplements and additional components are described above and may include L-glutamine or substitutes, such as GlutaMAX-1™, chemically defined lipids, albumin, 1-thiolglycerol, polyvinyl alcohol, insulin, nicotinamide, dexamethasone, selenium, pyruvate, buffers, such as HEPES, sodium bicarbonate, glucose, antibiotics such as penicillin and streptomycin, and transferrin.

Suitable chemically defined nutrient media for use in the endoderm induction medium include CDM-PVA and CDM-BA as described above.

A preferred endoderm induction medium may consist of CDM-PVA as described above supplemented with Activin-A (10 ng/mL to 1 ug/mL, preferably 100 ng/mL), BMP4 (1 to 100 ng/mL, preferably 10 ng/mL), bFGF (2 to 200 ng/ml preferably 20 ng/mL), CHIR99021 (0.3 to 30 µM, preferably 3 µM) and LY294002 (1 to 100 µM, preferably 10 µM).

The PSCs may be cultured in the endoderm induction medium for 1 to 6 days, preferably about 3 days, to produce a population of DECs.

DECs may express one or more, preferably all of Sox17, foxA2, GSC, Mixl1, Lhx1, CXCR4, GATA4, eomesodermin (EOMES), Mixl1, HNF-3 beta, Cerberus, OTX4, goosecoid, C-kit, CD99, and Hex. Typically, DECs are characterised by the expression of CXCR4 and Sox17.

DECs may lack markers associated with specific endodermal lineages for example gut, pancreas, liver or lung markers. For example, DECs may not express SOX2 (foregut), CDX2 (mid-hind gut), PDX1, PTF1a (pancreas). AFP (liver), Nkx2.1 or TBX1 (lung). DECs may also lack markers associated with pluripotency, such as Oct4, Sox2, Alkaline Phosphatase, POU5f1, SSEA-3, Nanog, SSEA-4, Tra-1-60, KLF-4 and c-myc, as well as markers associated with extraembryonic, mesoderm or neuroectoderm cell lineages.

The population of DECs is cultured in a foregut induction medium to produce the population of FSCs.

In preferred embodiments, the foregut induction medium is a chemically defined medium comprising a TGFβ ligand.

The foregut induction medium may be devoid of differentiation factors other than the TGFβ ligand. For example, the foregut induction medium may consist of a chemically defined nutrient medium supplemented with an effective amount of a TGFβ ligand. In some embodiments, the foregut induction medium may consist of a chemically defined nutrient medium supplemented with a TGFβ ligand, such as activin.

Suitable chemically defined nutrient media are described in more detail above. For example, a foregut induction medium may comprise a basal medium, such as RPMI, supplemented with a serum free medium supplement, such as B27.

The TGFβ ligand may be present in the medium in an effective amount, for example at 5 to 500 ng/mL, preferably 50 ng/mL.

A preferred foregut induction medium may consist of RPMI basal medium supplement with B27 and 50 ng/mL Activin-A.

The DECs may be cultured in the foregut induction medium for 5 to 7 days, preferably 6 days to allow the DECs to differentiate into FSCs.

FSCs may express one or more, preferably all of HNF4α, SOX17, CXCR4, EpCAM, HNF1β, GATA4, Cer, HNF6, HNF1beta, SOX2, HHEX, and HOXA3. For example, at least 50%, at least 60% or at least 70% of the cells in the population may express SOX2, HHEX, and HOXA3.

FSCs may lack expression of CDX2 or HOXC5. FSCs may also lack expression of pluripotency markers, such as Oct4, Sox2, alkaline phosphatase, SSEA-3, Nanog, SSEA-4, Tra-1-60, KLF-4 and POU5f1, and markers associated with ectodermal or mesodermal lineages. FSCs may lack expression of endodermal tissue markers, for example pulmonary markers, such as NKX2.1, hepatic markers, such as AFP, or pancreatic markers, such as PDX1 markers.

Methods of the invention relate to the in vitro differentiation of FSCs into CPs. FSCs are differentiated into CPs in a two-stage process. First, the population of FSCs is induced to differentiate into a population of hepatoblasts (HBs). The HBs are then induced to differentiate into CPs.

In order to produce the population of hepatoblasts (HBs), the population of FSCs is cultured in a hepatic induction medium comprising bone morphogenetic protein (BMP) and a TGFβ signalling inhibitor.

In preferred embodiments, the hepatic induction medium is a chemically defined medium comprising BMP and a TGFβ signalling inhibitor.

The hepatic induction medium may be devoid of differentiation factors other than BMP and the TGFβ signalling inhibitor.

The hepatic induction medium may consist of a chemically defined nutrient medium supplemented with an effective amount of BMP and TGFβ signalling inhibitor. For example, the hepatic induction medium may consist of a chemically defined nutrient medium supplemented with BMP4 and SB-431542.

The chemically defined nutrient medium may comprise or consist of a basal medium, such as RPMI, Advanced DMEM, or HCM™ Hepatocyte culture medium (Lonza Inc., USA) supplemented with one or more additional defined components as described above. Suitable chemically defined basal media for use in the hepatic induction medium are described above and include RPMI supplemented with a serum free medium supplement, such as B27. A preferred hepatic induction medium may consist of RPMI, supplemented with a serum free medium supplement, such as B27 as described above, supplemented with SB-431542 (1 to 100 µM, preferably µM) and BMP4 (1 to 100 ng/mL, preferably 50 ng/mL)

The FSCs may be cultured in the hepatic induction medium for 2 to 6 days to produce the population of HBs, preferably about 4 days.

HBs may express one or more, preferably all of the following markers: AFP, HNF4A, HNF1B, TBX3, and CK19. Preferably, the HBs are bi-potent and are capable of differentiation into hepatic or biliary lineages.

To produce the population of CPs, the population of HBs is cultured in a biliary induction medium comprising fibroblast growth factor (FGF), retinoic acid and a TGFβ ligand.

In preferred embodiments, the biliary induction medium is a chemically defined medium comprising fibroblast growth factor (FGF), retinoic acid and a TGFβ ligand.

The biliary induction medium may be devoid of differentiation factors other than fibroblast growth factor (FGF), retinoic acid and TGFβ ligand. For example, the biliary induction medium may consist of a chemically defined nutrient medium supplemented with fibroblast growth factor (FGF), retinoic acid and TGFβ ligand. Preferably, the TGFβ ligand is activin.

The chemically defined nutrient medium may comprise or consist of a basal medium supplemented with one or more additional defined components, such as polyvinyl alcohol, 1-thioglycerol, insulin, transferrin and defined lipids or a serum free medium supplement, such as B27, as described above. Suitable chemically defined basal media for use in the biliary induction medium are described above and include RPMI, William's E, Advanced DMEM, DMEM or DMEM/F12.

A preferred biliary induction medium may consist of RPMI, supplemented with a serum free medium supplement, such as B27 as described above, and further supplemented with FGF10 (1 to 100 ng/ml, preferably 50 ng/ml), activin (1 to 100 ng/ml, preferably 50 ng/ml) and RA (0.3 µM to 30 µM, preferably 3 µM).

The HBs may be cultured in the biliary induction medium for 2 to 6 days to produce the population of cholangiocyte progenitors (CPs), preferably about 4 days.

Preferably, the population of CPs is homogeneous or substantially homogeneous. For example, more than 50%, more than 60% or more than 70% of the cells in the population may be CPs, following culture in the hepatic induction medium.

CPs may express one or more, preferably all of the following markers: CK19, HNF1B, Sox9, Notch2 and Hes1.

CPs may lack expression of one or more, preferably all of the following markers: AFP, HNF4A, and TBX3, CPs may display gamma-glutamyltransferase (GGT) activity, Following generation, the population of CPs may be maintained, expanded or stored using conventional techniques.

The population of CPs may be useful, for example, for cell-based therapy or modelling early biliary development as described below.

Methods of the invention may further comprise maturing CPs generated as described above to produce a population of cholangiocyte-like cells (CLCs).

The CPs may be cultured in a cholangiocyte maturation medium comprising epidermal growth factor to produce the population of CLCs.

Preferably, the CPs are matured in the cholangiocyte maturation medium in three-dimensional cell culture to produce the population of CLCs.

For example, a method for producing a population of cholangiocyte-like cells (CLCs) may comprise:
(i) culturing population of foregut stem cells (FSCs) in a hepatic induction medium comprising bone morphogenetic protein (BMP) and a TGFβ signalling inhibitor (activin/TGFβ antagonist) to produce a population of hepatoblasts,
(ii) culturing the hepatoblasts in a biliary induction medium comprising fibroblast growth factor (FGF), retinoic acid and a TGFβ ligand to produce a population of cholangiocyte progenitors (CPs) and
(iii) culturing the CPs in a three-dimensional culture in cholangiocyte maturation medium comprising epidermal growth factor to produce a population of CLCs.

Preferably, the population of cholangiocyte-like cells (CLCs) matured from the CPs may form one or more organoids i.e. three dimensional multicellular structures comprising an interior lumen.

CLC-organoids may display cilia and tubular structures by electron microscopy, in addition to the functionality described herein.

In some embodiments, the cholangiocyte maturation medium may be a chemically defined medium. In other embodiments, the cholangiocyte maturation medium may comprise one or more components that are not chemically defined. For example, the medium may comprise a scaffold matrix which is not chemically defined, such as a complex protein hydrogel.

In preferred embodiments, the cholangiocyte maturation medium comprises a nutrient medium supplemented with epidermal growth factor.

Optionally, the cholangiocyte maturation medium may further comprise a Notch ligand and a TGFβ ligand. In some embodiments, the medium may be supplemented with the Notch ligand and the TGFβ ligand. In other embodiments, the Notch ligand and the TGFβ ligand may be present in an undefined scaffold matrix, for example a complex protein hydrogel, such as Matrigel™.

For example, the nutrient medium may consist of a basal medium supplemented with epidermal growth factor (EGF).

Suitable basal media may comprise or consist of a standard basal medium, such as Advanced DMEM or William's E medium, supplemented with one or more additional components, such as nicotinamide, sodium bicarbonate, phospho-L-ascorbic acid trisodium salt, sodium pyruvate, glucose, HEPES, insulin, human transferrin, linoleic acid and selenous acid (e.g. ITS+ premix), dexamethasone, glutamine or L-alanyl-L-glutamine (e.g. Glutamax™) and antibiotics, such as penicillin and streptomycin.

For example, the basal medium may be supplemented with 10 mM nicotinamide, 17 mM sodium bicarbonate, 0.2 mM 2-phospho-L-ascorbic acid trisodium salt, 6.3 mM sodium pyruvate, 14 mM glucose, 20 mM HEPES, 6 µg/ml insulin, human 6 µg/ml transferrin, 6 ng/ml selenous acid, 5 µg/ml linoleic acid, 0.1 uM dexamethasone, 2 mM L-alanyl-L-glutamine, 100 U/ml penicillin, 100 µg/ml streptomycin.

Preferably, the basal medium in the cholangiocyte maturation medium is William's E medium. A preferred nutrient medium may consist of William's E medium with the above supplements, and further supplemented with epidermal growth factor (EGF) (2 to 200 ng/ml, preferably 20 ng/ml).

The CPs may be cultured in two-dimensional culture in the cholangiocyte maturation medium. More preferably, the CPs are cultured in three-dimensional culture in the cholangiocyte maturation medium.

For three-dimensional cell culture, the cholangiocyte maturation medium may further comprise a scaffold matrix which supports the growth and proliferation of cells in 3-dimensions and allows the formation of organoids.

Suitable scaffold matrices are well-known in the art and include hydrogels, such as collagen, collagen/laminin, compressed collagen (e.g. RAFT™, TAP Biosystems), alginate, agarose, complex protein hydrogels, such as Base Membrane Extracts, and synthetic polymer hydrogels, such as polyglycolic acid (PGA) hydrogels and inert matrices, such as porous polystyrene.

The scaffold matrix may be chemically defined, for example a compressed collagen hydrogel, or non-chemically defined, for example a complex protein hydrogel.

Preferably, the scaffold matrix in the cholangiocyte maturation medium is a complex protein hydrogel. Suitable complex protein hydrogels may comprise extracellular matrix components, such as laminin, collagen IV, enactin and heparin sulphate proteoglycans.

Suitable complex protein hydrogels may include hydrogels of extracellular matrix proteins from Engelbreth-Holm-Swarm (EHS) mouse sarcoma cells. Suitable complex protein hydrogels are available from commercial sources and include Matrigel™ (Corning Life Sciences) or Cultrex™ BME 2 RGF (Amsbio™ Inc).

The cholangiocyte maturation medium may consist of a scaffold matrix and a nutrient medium supplemented with epidermal growth factor, as described above.

The CPs may be cultured in the cholangiocyte maturation medium for 5 to 15 days to produce the population of cholangiocyte-like cells (CLCs), preferably about 10 days.

Preferably, the population of CLCs is homogeneous or substantially homogeneous. For example, more than 50%, more than 60% or more than 70% of the cells in the population may be CLCs, following said culture.

Preferably, the population of CLCs forms one or more organoids during maturation.

Following maturation, the one or more organoids formed by the population of CLCs may be plated in 2-dimensional cell culture.

In some embodiments, the one or more organoids may be disrupted to allow isolation of CLCs. This may be useful, for example for FACS analysis, as described herein. Suitable methods for the disruption of organoids are well known in the art.

The CLCs express Sox9 and CK7, preferably SSTR2, ALP, CK7 CK19, GGT and SOX9.

The CLCs may express one or more, preferably all of the following mature biliary markers: CK7, CK18, CK19, HNF1B, Gamma Glutamyl-Transferase (GGT), Jagged 1 (JAG1), NOTCH2, CFTR, SCR, SSTR2, Apical Salt and Bile Transporter (ASBT), Aquaporin 1 and Anion Exchanger 2. Other biliary markers expressed by CLCS are shown in Table 2.

Preferably, the CLCs express mature biliary markers at levels corresponding to primary common bile duct (CBD) cholangiocytes.

The CLCs may display a gene expression profile that closely resembles the gene expression profile of primary common bile duct (CBD) cholangiocytes. For example, expression of the 21 cholangiocyte-specific genes of key biliary markers shown in Table 2 may be at similar levels in CLCs and primary common bile duct (CBD) cholangiocytes.

A population of CLCs produced by the claimed methods may contain at least 50%, at least 60% or at least 70% large CLCs (Glaser et al 2006 *World J Gastroenterol.*, 12:3523-36).

The expression of one or more CLC markers may be monitored and/or detected in the population of CLCs. For example, the expression or production of one or more of the mature biliary markers set out above in the population of CLCs may be determined. This allows the extent of differentiation in the population of CLCs to be determined and/or monitored.

CLCs produced as described herein may display one or more functional properties of primary common bile duct (CBD) cholangiocytes. For example, the CLCs may display one or more, preferably all of the properties set out in Table 1 and described below.

The CLCs may display the morphology or physical characteristics of primary common bile duct (CBD) cholangiocytes. A CLC organoid may comprise cilia and/or tubular structures. Morphology and physical characteristics may be determined by standard microscopic procedures.

The CLCs may display bile acid transfer, alkaline phosphatase (ALP) activity and/or Gamma-Glutamyl-Transpeptidase (GGT) activity. The amount of ALP and GGT activity may correspond to the amount of ALP and GGT activity displayed by primary common bile duct (CBD) cholangiocytes. ALP and GGT activity may be determined, for example, as described herein.

The CLCs may display active secretion, for example, secretion mediated by multidrug resistance protein-1 (MDR1). This may be determined by measuring the accumulation of a fluorescent MDR1 substrate, such as Rhodamine123, in the lumen of CLC organoids in the presence and absence of MDR1 inhibitor verapamil, as described herein.

The CLCs may display responses to secretin and somatostatin. For example, the CLCs may display increased secretory activity in response to secretin and decreased activity in response to somatostatin. This may be determined by measuring changes in CLC organoid size. For example, secretin may increase and somatostatin may decrease the size of CLC organoids.

The CLCs may display active export of bile acids, for example export mediated by Apical Salt and Bile Transporter (ASBT). Bile acid export activity may be determined, for example, by measuring the active export of a fluorescent bile salt, such as CLF, relative to another fluorescent compound, such as FITC, as described herein.

The CLCs may display Cystic Fibrosis Transmembrane Conductance Regulator (CFTR) activity. CTFR activity may be determined by measuring intracellular and intraluminal chloride concentrations in response to media with varying chloride concentrations, for example, the fluorescent chloride indicator N-(6-methoxyquinolyl) acetoethyl ester (MQAE), as described herein.

The CLCs may display responses to ATP and acetylcholine. For example, intracellular $Ca^{2+}$ levels may increase in the CLCs in response to ATP or acetylcholine. Intracellular $Ca^{2+}$ levels may be determined using standard techniques.

The CLCs may display responses to Vascular Endothelial Growth Factor (VEGF), Mitogens such as IL6, and oestrogens. For example, the CLCs may display increased proliferation in response to VEGF.

The CLCs may display responses to drugs, such as lumacaftor (VX809). For example, organoid size, CFTR activity and/or intraluminal fluid secretion may increase in the CLCs in response to lumacaftor. Suitable methods for determining responses to lumacaftor are described below.

The amount of response and/or activity of the CLCs produced by the claimed methods may correspond to the amount of response and/or activity displayed by primary common bile duct (CBD) cholangiocytes As described above, iPSCs derived from an individual with a biliary disorder may be used to generate CLCs which display a phenotype associated with a biliary disorder. For example, CLCs may display an undifferentiated phenotype which is associated with Alagille syndrome. An undifferentiated phenotype may be characterised by a lack of organoid formation or tubulogenesis.

In some embodiments, a method of producing CLCs with a biliary disorder-associated phenotype may comprise;
  providing a population of FSCs produced from biliary disorder specific iPSCs.
  inducing in vitro cholangiocytic differentiation of the FSCs into CPs and
  maturing the CPs into CLCs, as described herein,
  thereby producing a population of CLCs with a biliary disorder-associated phenotype.

In other embodiments, a method of producing CLCs with a biliary disorder-associated phenotype may comprise;
  providing a population of FSCs produced from normal iPSCs,
  inducing in vitro cholangiocytic differentiation of the FSCs into CPs and
  maturing the CPs into CLCs, as described herein, and
  treating the CLCs with a compound which induces a biliary disorder-associated phenotype in the cells,
  thereby producing a population of CLCs with a biliary disorder-associated phenotype.

A compound which induces a biliary disorder-associated phenotype may modulate e.g. activate or inhibit, a cellular pathway that is associated with the biliary disorder.

In some embodiments, the CLCs may be co-cultured with one or more other cell types to elicit a biliary disorder-associated phenotype. For example, the CLCs may be co-cultured with immune cells, such as T-cells, to elicit a phenotype associated with an autoimmune biliary disorder, such as Primary Biliary Cirrhosis (PBC).

Once produced, CLCs with the biliary disorder-associated phenotype may be cultured, expanded and maintained, for example for use in screening.

CLC with a biliary disorder-associated phenotype may display one or more properties, features or pathologies characteristic of the biliary disorder.

Biliary disorders may include cholangiopathies, for example inherited, developmental, autoimmune and environment-induced cholangiopathies, such as Cystic Fibrosis associated cholangiopathy, Alagille Syndrome, polycystic liver disease, primary biliary cirrhosis, primary sclerosing cholangitis, AIDS associated cholangiopathy, disappearing bile duct syndrome, and biliary atresia.

Following the production of a population of CLCs with a biliary disorder-associated phenotype as described above, a method may comprise detecting or measuring one or more disease-pathologies in the population.

Disease pathologies may include one or more of aberrant bile acid transfer, aberrant ATP or acetylcholine responses, increased apoptosis, lack of organoid formation or tubulogenesis, aberrant gene expression; aberrant response to VEGF; protein aggregation or polymerisation; protein entrapment in the ER; ALP or GT activity; aberrant responses to secretin or somatostatin; aberrant CFTR activity or aberrant MDR1 activity relative to normal cells.

Suitable methods of measuring functional properties and disease pathologies are described elsewhere herein.

A population of CPs or CLCs generated as described herein may be substantially free from other cell types. For example, the population may contain 70% or more, 80% or more, 85% or more, 90% or more, or 95% or more CPs or CLCs, following culture in the medium. The presence or proportion of CPs or CLCs in the population may be determined through the expression of biliary markers as described above.

Preferably, the population of CPs or CLCs is sufficiently free of other cell types that no purification is required. If required, the population of CPs or CLCs may be purified by any convenient technique, including FACS.

A population of CLCs generated as described herein may be in the form of organoids or individual cells The ability of CPs or CLCs generated as described herein to perform one or more cholangiocyte functions may be monitored and/or determined. For example, the ability of the cells to perform one or more of MDR1 function; bile acid transfer VEGF, acetylcholine or ATP responses; CFTR mediated chloride transport; or secretin or somatostatin responses may be monitored and/or determined.

CPs, CLCs and CLC-organoids produced as described herein may be expanded, cultured or maintained using standard mammalian cell culture techniques.

In some embodiments, the population of CPs or CLCs produced as described herein may be stored, for example by lyophilisation and/or cryopreservation.

The population of CPs or CLCs may be admixed with other reagents, such as buffers, carriers, diluents, preservatives, pharmaceutically acceptable excipients and/or biodegradable cell scaffolds. Suitable reagents are described in more detail below. A method described herein may comprise admixing the population of CPs or CLCs with a therapeutically acceptable excipient and/or a biodegradable cell scaffold.

Another aspect of the invention provides a population of isolated CPs or CLCs generated by a method described herein or an organoid comprising CLCs generated by a method described herein.

The population may contain 70% or more, 80% or more, 85% or more, 90% or more, or 95% or more CPs or CLCs.

CLCs generated as described herein may be in the form of organoids or isolated cells.

CLCs produced by the methods described herein may display one or more functions or functional characteristics specific to primary common bile duct cholangiocytes. For example, the CLCs may display the MDR1 function; bile acid transfer, VEGF, acetylcholine or ATP responses; CFTR mediated chloride transport; gamma-glutamyl transferase (GGT) activity, alkaline phosphatase (ALP) activity, secretin or somatostatin responses or responses to drugs of primary common bile duct cholangiocytes.

For therapeutic applications, the CPs or CLCs are preferably clinical grade cells. Populations of CLCs for use in treatment are preferably produced from CPs as described herein using a chemically defined cholangiocyte maturation medium. CPs administered to an individual may differentiate in vivo into CLCs.

The population of CPs or CLCs may be transplanted, infused or otherwise administered into the individual. Preferably, the CPs or CLCs are incorporated in biodegradable scaffolds for administration. Suitable techniques are well known in the art.

The population of CPs or CLCs may be produced from iPSCs derived from cells obtained from the individual (i.e. autologous cells). In some embodiments, disease associated mutations or genetic defects in the iPSCs may be corrected before differentiation into CPs or CLCs, as described above.

Aspects of the invention provide a population of CPs or CLCs for use in the method of treatment of the human or animal body, for example, the treatment of a biliary disorder, such as a cholangiopathy; the use of a population of CPs or CLCs in the manufacture of a medicament for use in the treatment of a biliary disorder, for example a biliary disorder described above; and a method of treating a biliary disorder may comprise administering a population of isolated CPs or CLCs to an individual in need thereof.

Aspects of the invention also extend to a pharmaceutical composition, medicament, drug or other composition comprising CPs or CLCs produced as described herein, a method comprising administration of such CPs or CLCs to a patient, e.g. for treatment (which may include preventative treatment) of a biliary disorder, as described above, and a method of making a pharmaceutical composition comprising admixing such CPs or CLCs with a pharmaceutically acceptable excipient, vehicle, carrier or biodegradable scaffold, and optionally one or more other ingredients.

In particular, biliary disorders may include disorders characterised by damage to or destruction of bile ducts, aberrant bile ducts or the absence of bile ducts, such as vanishing bile duct syndrome, biliary atresia or Alagille syndrome.

A pharmaceutical composition containing CPs or CLCs produced in accordance with the invention may comprise one or more additional components. Pharmaceutical compositions may comprise, in addition to the CPs or CLCs, a pharmaceutically acceptable excipient, carrier, buffer, preservative, stabiliser, anti-oxidant, biodegradable scaffold or other material well known to those skilled in the art. Such materials should be non-toxic and should not interfere with the activity of the CPs or CLCs. The precise nature of the carrier or other material will depend on the route of administration.

Liquid pharmaceutical compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

CPs or CLCs or scaffolds comprising CPs or CLCs may be implanted into a patient by any technique known in the art (e.g. Lindvall, O. (1998) Mov. Disord. 13, Suppl. 1:83-7; Freed, C. R., et al., (1997) Cell Transplant, 6, 201-202; Kordower, et al., (1995) New England Journal of Medicine, 332, 1118-1124; Freed, C. R., (1992) New England Journal of Medicine, 327, 1549-1555, Le Blanc et al, Lancet 2004 May 1; 363(9419):1439-41). In particular, cell suspensions may be injected into the bile duct, portal vein and liver of a patient.

Administration of a composition in accordance with the present invention is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors.

A composition comprising CPs or CLCs may be administered alone or in combination with other treatments, either simultaneously or sequentially dependent upon the condition to be treated.

In some embodiments, the CPs or CLCs in the population produced as described herein may display a normal phenotype. For example, cells may be obtained from an individual with a biliary disorder and used to produce iPS cells. In some embodiments, the iPS cells may contain a mutation or genetic defect and this mutation or defect may be corrected using conventional recombinant techniques to produce iPS cells with a normal phenotype. Alternatively, iPS cells with a normal genotype may be obtained from the individual with the biliary disorder. CPs or CLCs with a normal phenotype may be produced from these iPS cells as described herein and implanted into the patient to repair or ameliorate the disorder.

In other embodiments, the CPs or CLCs in the population produced as described herein may display a disease phenotype. For example, cells may be obtained from an individual with a biliary disorder and used to produce disease-specific iPS (ds-IPS) cells. CPs or CLCs progenitors with a disease phenotype may be produced from these iPS cells as described herein. These cells may then be treated to restore a normal phenotype. For example, the genetic mutation or defect which is responsible for the disease phenotype may be corrected in vitro. Various techniques are available to correct genetic mutations or defects in isolated mammalian cells. Once the defect or mutation is corrected and the normal phenotype restored, the CPs or CLCs may be implanted into the patient to repair or ameliorate the disorder.

Populations of isolated CPs or CLCs produced as described above may be useful in modelling the interaction of test compounds with cholangiocytes, for example in toxicity screening, modelling biliary disorders or screening for compounds with potential therapeutic effects.

CLCs for use in modelling and screening may be in the form of organoids or isolated cells produced, for example by disruption of CLC organoids.

Suitable isolated CPs or CLCs for use in screening and modelling include cells having a normal genotype and phenotype and cells having disease associated genotype or phenotype, for example a genotype or phenotype associated with a biliary disorder.

A method of screening a compound may comprise
  contacting a population of isolated CPs or CLCs generated as described herein with a test compound, and;
  determining the effect of the test compound on said CLCs or CPs and/or the effect of said CLCs or CPs on the test compound.

The proliferation, growth, viability or bile acid resistance of CPs or CLCs, or their ability to differentiate or perform one or more cell functions may be determined in the presence relative to the absence of the test compound.

A decrease in differentiation, proliferation, growth, viability or ability to perform one or more cell functions is indicative that the compound has a toxic effect and an increase in growth, viability or ability to perform one or more cell functions is indicative that the compound has an ameliorative effect on the CPs or CLCs.

The CPs or CLCs may display a normal or a disease phenotype.

Gene expression may be determined in the presence relative to the absence of the test compound. For example, the expression of one or more genes listed in Table 2 may be determined. Combined decrease in expression is indicative that the compound has a toxic effect or can modify the functional state of the CPs or CLCs. Gene expression may be determined at the nucleic acid level, for example by RT-PCR, or at the protein level, for example, by immunological techniques, such as ELISA, or by activity assays. Cytochrome p450 assays, for example, luminescent, fluorescent or chromogenic assays are well known in the art and available from commercial suppliers.

In some embodiments, the expression of risk loci for a biliary disease, such as PSC, may be determined.

The metabolism, degradation, or breakdown of the test compound by the CPs or CLCs may be determined. In some embodiments, changes in the amount or concentration of test compound and/or a metabolite of said test compound may be determined or measured over time, either continuously or at one or more time points. For example, decreases in the amount or concentration of test compound and/or increases in the amount or concentration of a metabolite of said test compound may be determined or measured. In some embodiments, the rate of change in the amount or concentration of test compound and/or metabolite may be determined. Suitable techniques for measuring the amount of test compound or metabolite include mass spectrometry.

This may be useful in determining the in vivo half-life, toxicity, efficacy or other in vivo properties of the test compound.

One or more functions of the CPs or CLCs may be determined and/or measured in the presence relative to the absence of the test compound. For example, the ability of the CLCs to perform one or more of MDR1 function; bile acid transfer, VEGF, acetylcholine or ATP responses; CFTR mediated chloride transport; GGT activity, ALP activity or secretin or somatostatin responses may be determined and/or measured. The ability of the CPs to mature into CLCs or CLC-organoids may be determined.

A decrease in the ability of the CLCs or CPs to perform one or more of these functions in the presence relative to the absence of the test compound is indicative that the compound has a toxic effect. An increase in the ability of the CLCs or CPs to perform one or more of these functions in the presence relative to the absence of the test compound is indicative that the compound has a pro-biliary effect (e.g. it promotes biliary specification). For example, a test compound that has a pro-biliary effect in CLCs or CPs with genetic defects associated with a biliary disorder may be identified.

A method of screening for a compound useful in the treatment of a biliary disorder may comprise;
  contacting a population of CLCs or CPs produced as described above with a test compound, and;
  determining the effect of the test compound on said CLCs or CPs.

The CLCs or CPs may display a biliary disorder phenotype. The effect of the test compound on one or more disease pathologies in the CLCs or CPs may be determined. For example, the effect of the test compound on one or more of cell growth, gene expression, organoid formation or tubulogenesis, protein aggregation or polymerisation; GGT activity, ALP activity, MDR1 function; bile acid transfer; VEGF, acetylcholine or ATP responses; CFTR mediated chloride transport; secretin or somatostatin responses or antigen presentation by the CLCs or CPs may be determined. Suitable techniques for determining the effect of the test compound are well known in the art and include immunostaining, mass spectrometry, Western blots, and enzymatic assays.

Preferably, a population of CLCs is contacted with the test compound.

A decrease or amelioration of one or more disease pathologies in the CPs or CLCs in the presence, relative to the absence of test compound may be indicative that the test compound may be useful in the treatment of a biliary disorder. Examples of biliary disorders are provided above.

In some embodiments, an increase in CFTR mediated chloride transport in a population of CPs or CLCs may be indicative that the test compound may be useful in the treatment of Cystic Fibrosis or a CF-associated cholangiopathy.

In some embodiments, an increase in biliary specification in a population of CPs may be indicative that the test compound may be useful in the treatment of a biliary disorder associated with reduced biliary development, such as Alagille Syndrome (AGS).

Methods as described herein may comprise the step of identifying a test compound which reduces or ameliorates one or more disease pathologies, in the CLCs or CPs. Compounds which reduce disease pathologies may be useful in the development of therapeutics for the treatment of the biliary disorder.

In other embodiments, the CLCs or CPs may display a normal phenotype and may, for example, be derived from an individual with a high risk of or high susceptibility to biliary disorders, relative to the general population. The effect of the test compound on one or more of cell growth, or gene expression, for example expression of a gene shown in Table 2, may be determined. The effect of the test compound on one or more functions of the CLCs may be determined. For example, the ability of the CLCs to perform one or more of MDR1 function; bile acid transfer; VEGF, acetylcholine or ATP responses; CFTR mediated chloride transport; and secretin or somatostatin responses, may be determined and/or measured in the presence relative to the absence of the test compound.

An increase in gene expression, growth, efficiency of organoid formation and/or one or more functions in the presence relative to the absence of the test compound may be indicative that the compound may be useful in the treatment of a biliary disorder.

Following identification of a compound which reduces or ameliorates one or more disease pathologies in the CLCs, the compound may be modified to optimise its pharmaceutical properties. This may be done using modelling techniques which are well-known in the art.

A test compound identified using one or more initial screens as having ability to reduce or ameliorate one or more disease pathologies, in the CLCs may be assessed further using one or more secondary screens. A secondary screen may involve testing for a biological function or activity in vitro and/or in vivo, e.g. in an animal model. For example, the ability of a test compound to reduce or ameliorate one or more symptoms or pathologies associated with the biliary disorder in an animal model of the disease may be determined.

Following identification of a test compound which reduces or ameliorates one or more disease pathologies in the CLCs or CPs, the compound may be isolated and/or purified or alternatively it may be synthesised using conventional techniques of recombinant expression or chemical synthesis. Furthermore, it may be manufactured and/or used in preparation, i.e. manufacture or formulation, of a composition such as a medicament, pharmaceutical composition or drug. These may be administered to individuals for the treatment of a biliary disorder.

Populations of isolated CPs or CLCs produced as described above may also be useful in methods of diagnostic testing, for example to identify the presence of a biliary disorder in an individual.

A method of testing an individual for a biliary disorder may comprise
  producing a population of iPSCs from a sample of cells obtained from the individual,
  producing a population of isolated CPs or CLCs from the iPSCs using a method described above; and
  determining the phenotype of the isolated CPs or CLCs.

The presence of a disease associated phenotype in the CPs or CLCs may be indicative that the individual has a biliary or other disorder. For example, the presence of deficiencies or aberrations in one or more of cell growth, gene expression, protein aggregation or polymerisation; organoid formation or tubulogenesis, GGT activity, ALP activity, MDR1 function; bile acid transfer; VEGF, acetylcholine or ATP responses; CFTR mediated chloride transport; secretin or somatostatin responses or antigen presentation may be indicative that the individual has a biliary disorder. In some embodiments, gene expression in risk loci for PBC may be determined.

In some embodiments, the method may be useful in prenatal screening. For example, a method of pre-natal testing for Alagille syndrome may comprise
  producing a population of iPSCs from a sample of cells obtained from an unborn foetus,
  producing a population of isolated CPs or CLCs from the iPSCs using a method described above; and determining the ability of the isolated CPs or CLCs to form organoids.

An inability or deficiency in the formation of organoids by the CPs or CLCs may be indicative of the presence of Alagille syndrome in the unborn foetus.

Other aspects of the invention provide kits and reagents for use in generating populations of CPs and CLCs using the methods described above.

A kit for production of CPs or CLCs may comprise;
a hepatic induction medium comprising bone morphogenetic protein (BMP) and a TGFβ signalling inhibitor,
a biliary induction medium comprising fibroblast growth factor (FGF), retinoic acid and a TGFβ ligand, and optionally
a cholangiocyte maturation medium comprising epidermal growth factor.

The kit may further comprise an endoderm induction medium and a foregut induction medium as described above.

The kit may further comprise a scaffold matrix, such as Matrigel™. The scaffold matrix may be provided as part of the cholangiocyte maturation medium or may be provided separately.

An aspect of the invention also provides the use of a set of culture media for the production of CLCs, wherein the set of media comprises;
a hepatic induction medium comprising bone morphogenetic protein (BMP) and a TGFβ signalling inhibitor,
a biliary induction medium comprising fibroblast growth factor (FGF), retinoic acid and a TGFβ ligand, and optionally
a cholangiocyte maturation medium comprising epidermal growth factor.

The set of media may further comprise an endoderm induction medium and a foregut induction medium as described above.

Suitable hepatic induction, biliary induction, cholangiocyte maturation, endoderm induction and foregut induction media are described in more detail above.

Media may be supplemented with effective amounts of the differentiation factors set out above, as described elsewhere herein.

The one or more culture media may be formulated in deionized, distilled water. The one or more media will typically be sterilized prior to use to prevent contamination, e.g. by ultraviolet light, heating, irradiation or filtration. The one or more media may be frozen (e.g. at −20° C. or −80° C.) for storage or transport. The one or more media may contain one or more antibiotics to prevent contamination.

The one or more media may be a 1× formulation or a more concentrated formulation, e.g. a 2× to 250× concentrated medium formulation. In a 1× formulation each ingredient in the medium is at the concentration intended for cell culture, for example a concentration set out above. In a concentrated formulation one or more of the ingredients is present at a higher concentration than intended for cell culture. Concentrated culture media are well known in the art. Culture media can be concentrated using known methods e.g. salt precipitation or selective filtration. A concentrated medium may be diluted for use with water (preferably deionized and distilled) or any appropriate solution, e.g. an aqueous saline solution, an aqueous buffer or a culture medium.

The one or more media in the kit may be contained in hermetically-sealed vessels. Hermetically-sealed vessels may be preferred for transport or storage of the culture media, to prevent contamination. The vessel may be any suitable vessel, such as a flask, a plate, a bottle, a jar, a vial or a bag.

Lumacaftor (VX809) is shown herein to rescue the CF disease phenotype in the context of biliary disease.

Another aspect of the invention provides lumacaftor (VX809; 3-{6-{[1-(2,2-Difluoro-1,3-benzodioxol-5-yl)cyclopropanecarbonyl]amino}-3-methylpyrdin-2-yl}benzoic acid) for use in the treatment of a biliary disorder, for example a cholangiopathy such as CF-associated cholangiopathy, in an individual in need thereof.

Biliary disorders are described in more detail above. The individual may be suffering from cystic fibrosis or other disorder relating to CFTR activity.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

Table 1 shows a summary of the comparison between CLCs and the hESC-Chol cells generated by Dianat et al (6) "CBD" means Common Bile Duct cholangiocytes.

Table 2 shows the ranking of the expression of 21 genes for key biliary markers in CLCs vs. hESC-Chol generated by Dianat et al. (6) demonstrating higher expression in CLCs (Highest expression: Rank=1).

Experiments

Methods
Generation of hIPSC Lines

All the hIPSC lines used have been derived and characterized previously by our lab (9), therefore no new hIPSC lines were derived for this study. Briefly, the lines used were generated as previously described from human skin fibroblasts and peripheral blood (ethics reference no. 08/H0311/201 and 09/H0304/77 respectively), using the Yamanaka approach (4, 9). The CF fibroblasts were obtained from the Coriell cell repository. The lines were authenticated using SNIP arrays and regularly tested negative for *mycoplasma* contamination.

Culture of hIPSCs

Human iPS cells were maintained in defined culture conditions as previously described (9, 10, 46), using activin-A (10 ng/ml) and b-FGF (12 ng/ml).

Differentiation of hIPSCs into Cholangiocyte Progenitors.

hIPSCs were differentiated into Foregut Progenitor cells (FP) as previously described (46). Bipotent hepatoblasts were generated by culturing FPs in RPMI (Gibco, Invitrogen)+B27 supplemented with SB-431542 (10 µM, Tocris Bioscience) and BMP4 (50 ng/ml) for 4 days. To induce biliary specification hepatoblasts were cultured for another 4 days in the presence of RPMI (Gibco, Invitrogen)+B27 supplemented with FGF10 (50 ng/ml, Peprotech), activin-A (50 ng/ml) and RA (3 µM, Sigma-Aldrich).

Maturation of Cholangiocyte Progenitor Cells to Cholangiocyte Like Cells and Organoid Formation in 3D Culture Human CPs were passaged using Cell Dissociation Buffer (Gibco, Life Technologies) and suspended at a density of 8×104 cells/ml, in a mixture of 40% matrigel (BD Biosciences, catalogue number: 356237) and 60% William's E medium (Gibco, Life Technologies) supplemented with 10 mM nicotinamide (Sigma-Aldrich), 17 mM sodium bicarbonate (Sigma Aldrich), 0.2 mM 2-Phospho-L-ascorbic acid trisodium salt (Sigma-Aldrich), 6.3 mM sodium pyruvate (Invitrogen), 14 mM glucose (Sigma-Aldrich), 20 mM HEPES (Invitrogen), ITS+ premix (BD Biosciences), 0.1 uM dexamethasone (R&D Systems), 2 mM Glutamax (Invitrogen),100 U/ml penicillin per 100 µg/ml streptomycin and 20 ng/ml EGF (R&D Systems). A 50 µL droplet of the cell suspension was added in the centre of each well of a 24-well plate: the gel was allowed 2 hours at 37° C. to solidify and then overlaid with William's E medium with supplements. The medium was changed every 48 hours and the cells were cultured for a total of 10 days. Importantly, using the same methodology, we have been able to culture CLC organoids in multiple formats ranging from 6 to 96 well plates. To generate large numbers of CLC organoids, multiple 50 µL droplets were added in a well of a 6 well plate or a 10 cm dish. To provide a large number of wells compatible with high throughput screening and large scale experiments 30 µL droplets were added in a well of a 96 well plate. In both cases, the gel was allowed 2 hours at 37° C. to solidify and then overlaid with William's E medium with supplements.

Inhibition of Activin and Notch Signaling in 3D Culture and Assessment of Organoid Formation.

Human CPs were suspended at a density of 8×104 cells/ml, in a mixture of 40% matrigel and 60% William's E medium (Gibco, Life Technologies) with supplements as described above. The cell suspension was distributed in 3 equal volume aliquots. One aliquot received no further supplementation and was used as a positive control. The second aliquot was further supplemented by 10 µM SB-431542 for the inhibition of TGFβ/activin signaling. 501 µM of L-685,458 (Tocris Biosciences) were added in the third aliquot for the inhibition of Notch signaling. Each aliquot was distributed in 24-well plate format. The same concentrations of inhibitors were added to the medium overlaying the matrigel on a daily basis. After a total of 10 days in 3D culture, the total number of cysts in 4 random wells of a 24 well plate was counted for each condition by a blinded researcher. Error bars represent SD.

Flow Cytometry Analyses

HIPSCs, FPs, HBs and CPs were dissociated to single cells using Cell Dissociation Buffer (Life Technologies). The cells were subsequently counted using a hemocytometer and fixed using 4% PFA for 20 minutes at 4° C. Cell staining and flow cytometry analyses were performed as previously described (47).

CLC organoids were washed once with PBS and 1 ml of ice cold dispase was added per well of a 24 well plate. The matrigel was mechanically dissociated, transferred in a falcon tube and kept on ice to allow the combination of low temperature and dispase digestion to liquefy the matrigel. After 10 minutes, the cells were centrifuged at 1600 rpm for 3 minutes and the supernatant was aspirated. The pellet was washed once with PBS and the centrifugation step repeated. The supernatant was aspirated and 1 ml of TrypIE (Life technologies) was added for 3-5 minutes until the organoids were dissociated to single cells. Finally, the single cell suspension was centrifuged at 1600 rpm for 3 minutes, 1 and fixed using 4% PFA for 20 minutes at 4° C. Cell staining and flow cytometry analyses were performed as previously described (47).

Primary Cholangiocytes

Frozen primary human cholangiocytes derived from common bile duct were obtained from Celprogen (Catalogue Number 36755-11). The cells were thawed according to the manufacturer's instructions and lysed for RNA extraction.

Primary Biliary Tissue

Primary biliary tissue (bile duct) was obtained from an organ donor. The liver and pancreas from the donor were being retrieved for transplantation. A section of the bile duct was excised during the multi-organ retrieval operation after obtaining informed consent from the donor's family (REC reference number 09/H0306/73). The tissue was homogenized using a tissue homogenizer and RNA was extracted as previously described (9).

Immunofluorescence, RNA Extraction and Quantitative Real Time PCR

IF, RNA extraction and QPCR were performed as previously described (7). A complete list of the primary and secondary antibodies used is provided in supplementary table 5. A complete list of the primers used is provided in supplementary table 6. All QPCR data are presented as mean values of four independent biological replicates, with the exception of the primary CDB cholangiocytes from Celprogen, where 3 independent samples were used. Error bars represent SD.

For IF in 3D matrigel cultures, the organoids were fixed in matrigel with 4% PFA for 20 minutes at room temperature, to avoid matrigel liquefaction. The samples were permeabilized and blocked with 0.1% Triton-X and 10% donkey serum respectively 1 for 30 minutes and incubated with primary antibody in 1% donkey serum overnight at 4° C. The following day the samples were washed 3 times with PBS for 45 minutes per wash, incubated with secondary antibody in 1% donkey serum for 60 minutes at room temperature and washed again 3 times in PBS. Hoechst 33258 was added to the first wash. For RNA extraction in 3D matrigel cultures, the organoids were washed once with PBS and 1 ml of ice cold dispase was added per well of a 24 well plate. The matrigel was mechanically dissociated, transferred in a falcon tube and kept on ice to allow the combination of low temperature and dispase digestion to liquefy the matrigel. After 10 minutes the cells were centrifuged at 1600 rpm for 3 minutes and the supernatant was aspirated. The pellet was washed once with PBS and the centrifugation step repeated. Finally, the supernatant was aspirated and 350 µL of RNA lysis buffer were added to the pellet. RNA was extracted from the lysate using a kit (Sigma-Aldrich), according to the manufacturer's instructions.

Microarrays 500 ng of total cellular RNA was amplified and purified using the Illumina TotalPrep-96 RNA Amplification kit (Life Technologies) according to the manufacturer's instructions. Three biological replicates for each condition were analysed. Biotin-Labelled cRNA was then normalized to a concentration of 150 ng/µl and 750 ng were hybridised to Illumina Human-12 v4 BeadChips for 16 hours (overnight) at 58° C. Following hybridisation, BeadChips were washed and stained with streptavidin-Cy3 (GE Healthcare). BeadChips were then scanned using the BeadArray reader, and image data was then processed using Genome Studio software (Illumina). The raw and processed microarray data are available on ArrayExpress (Accession number: E-MTAB-2965).

Microarrays Analysis

Probe summaries for all arrays were obtained from the raw data using the method "Making Probe Summary". These values were transformed (variance stabilized) and quantile normalised using the R/Bioconductor package lumi (47). Standard lumi QC procedure was applied and no outliers were identified. Differential expression between pairs of conditions was evaluated using the R/Bioconductor package lumi (48). A linear model fit was applied, and the top differentially expressed genes were tabulated for each contrast using the method of Benjamini and Hochberg to correct the p-values (49). Probes that failed to fluoresce above background in both conditions were removed. Differentially expressed probes were selected using a cutoff of adjusted p value <0.01 and absolute fold-change >2. Probes differentially expressed between hIPSCs and CLCs or hIPSCs and HBs (representing the aggregate transcriptional "signature" of CLCs and HBs) were selected for Euclidean hierarchical clustering using Perseus software (MaxQuant). Standard scores (z-scores) of the log 2 normalized probe expression values across the different conditions were calculated and used for this analysis.

Rhodamine123 Transport Assay

CLC organoids were incubated with 100 µM of Rhodamine 123 (Sigma-Aldrich) for 5 minutes at 37° C. and the washed with William's E medium 3 times. Fresh William's E medium with supplements was added following the third wash. The organoids were incubated at 37° C. for another 40 minutes. To demonstrate that Rhodamine123 transfer indeed reflected the activity of the membrane channel MultiDrug Resistance Protein 1 (MDR1), CLCs were incubated with 10 µM of Verapamil (Sigma-Aldrich) at 37° C. for 30 minutes and the rhodamine assay was repeated. Following completion of each experiment, images were taken using a confocal microscope. Multiple fluorescence measurements were made (around 1000) between the organoid interior and exterior. Rhodamine123 fluorescence in the organoid lumen was normalized over background measured in the surrounding external area. Each experiment was repeated in triplicate. Error bars represent SD. Mean fluorescence intensity comparisons were performed using a two sided student's t-test.

Cholyl-Lysyl-Fluorescein Transport Assay

CLC organoids were loaded with 5 uM of Cholyl-Lysyl-Fluorescein (CLF, Corning Incorporated) for 30 minutes at 37° C. and the washed with Leibovitz's medium (Life technologies) 3 times. Following completion of the third wash, time lapse images were taken using a confocal microscope for 10 minutes. To demonstrate that the changes in CLF fluorescence intensity observed were secondary to active export of CLF from the organoid lumen, the experiment was repeated with 5 µM of unconjugated Fluorescein Isothiocyanate (FITC) (Sigma-Aldrich) as a control. Multiple fluorescence measurements were made (around 1000) between the organoid interior and exterior. Fluorescence in the organoid lumen was normalized over background measured in the surrounding external area. Each experiment was repeated in triplicate. Error bars represent SD. Mean fluorescence intensity comparisons were performed using a two sided student's t-test.

Measurement of Intracellular Calcium Levels

Intracellular calcium signaling, regulated by stimuli such as acetylcholine and ATP constitutes a key second messenger for cholangiocytes (18). CLC organoids were incubated with 25 µM of the calcium indicator Fluo-4 AM (Life technologies) for 60 minutes at 37° C. and washed 3 times with William's E medium. Fresh William's E medium with supplements was added following the third wash. The organoids were stimulated with 1 µM of Acetylcholine (Sigma-Aldrich) or 30 µM of ATP (Sigma-Aldrich), while time lapse images were taken. Each measurement was repeated in triplicate. To calculate the number of cells responding to stimulation, the number of cells loaded with Fluo-4 AM was counted by 2 different researchers prior to the start of the experiment. Following stimulation with ATP or acetylcholine the number of responding cells (increase in fluorescence) was also counted and responsiveness was expressed as the ratio of responding cells over the total number of cells loaded with Fluo-4 AM. The statistical approach for smoothing the data and plotting bands for the confidence limits please see 'Statistical analyses'.

Proliferation Assays

50 µL droplets of Matrigel, each containing 40,000 cells were distributed in 20 wells of a 24 well plate. VEGF at a concentration of 50 ng/ml was added to half of the wells with every media change. Following 5 days of culture the matrigel was digested with dispase as described above (RNA extraction section) and the organoids were mechanically dissociated to single cells. The number of cells for each well was then counted using a haemocytometer. 25 different measurements were made by a blinded researcher. Primary cholangiocytes distributed in 6 wells of a 12 well plate were used as a positive control. 3 wells received VEGF at a concentration of 50 ng/ml with every media change for 5 days after which, the number of cells in each well was counted as described above. Error bars represent SD. Mean cell number comparisons were performed using a two sided student's t-test.

GGT Activity

GGT activity was measured in triplicate using the MaxDiscovery™ gamma-Glutamyl Transferase (GGT) Enzymatic Assay Kit (Bioo scientific) based on the manufacturer's instructions. Mouse embryonic feeders were used as a negative control. The equivalent serum GGT activity in IU/L was calculated following the manufacturer's instructions by multiplying the average increase in absorbance over 10 minutes by 353. Error bars represent SD. Multiple mean absorbance comparisons (CLCs vs. substrate, CLCs vs. MEFs, CLCs vs. human serum) were performed using one-way ANOVA with Dunnett correction for multiple comparisons.

Alkaline Phosphatase Staining

Alkaline phosphatase was carried out using the BCIP/NBT Color Development Substrate (5-bromo-4-chloro-3-indolyl-phosphate/nitro blue tetrazolium) (Promega) according to the manufacturer's instructions.

Effect of Secretin, Somatostatin, Octreotide and VX809 on Organoid Size

Images of CLC organoids were taken using 5× magnification before and following the addition of secretin (100 nM, Sigma Aldrich), somatostatin (100 nM, Sigma Aldrich), octreotide (100 nM, Sigma Aldrich) or embryo transfer water serving as a negative control, at 0.5-2 minute intervals until organoid size stabilized. To explore the impact of octreotide on the effect of secretin, cells were pre-incubated for 3 1 0 minutes with octreotide. 100 nM of secretin (Sigma Aldrich) was subsequently added to the medium and the experiment was carried out as described above. To assess the effect of VX809 on organoid size images were taken before and 6 hours following the addition of VX809 (30 mM, Selleck) or embryo transfer water, serving as a negative control. 3 random diameters were measured for 8 random organoids pre and post treatment. Graph measurements represent percentage differences in mean organoid diameter. Error bars represent SD. Statistical significance was calculated using one-way ANOVA with Dunnett correction for multiple comparisons. The videos available as online supplementary data were made by taking images pre and post treatment at 2 minute intervals, until organoid size stabilized.

cAMP Levels cAMP levels were measured in triplicate using the cAMP-Glo assay kit (Promega) based on the manufacturer's instructions and a P450-Glomax 96 microplate luminometer (Promega). Error bars represent SD. Statistical significance was calculated using one-way ANOVA with Dunnett correction for multiple comparisons.

CFTR Activity

CFTR activity was measured as previously described. Briefly, MQAE is a fluorescent dye quenched by the presence of chloride but not affected by other anions or pH changes (36). Chloride transfer across the cell membrane is mainly regulated by CFTR in cholangiocytes. Therefore, cells with a functional CFTR will respond to a chloride challenge by rapidly increasing intracellular (and intraluminal in case of organoids) chloride concentration thereby quenching MQAE fluorescence. Chloride depletion using a nitrate solution will have the opposite effect. Cells were incubated with 8 mM MQAE fluorescent dye (Life Technologies) and 5 µM forskolin for 4 hours at 37° C. MQAE fluorescence is quenched in the presence chloride. Standard Ringers solution containing NaCl, KCl, CaCl, MgCl, glucose and hepes was used to provide a chloride challenge expected to increase intracellular chloride levels in the presence of functional CFTR. Modified Ringers solution consisting of $NaNO_3$, $KNO_3$, $CaNO_3$, $MgNO_3$, glucose and hepes was used to promote chloride efflux and deplete intracellular chloride. Live pictures were captured every minute as each solution was added. To demonstrate the effect of VX809 on CFTR functionality, CLC organoids were incubated with 30 mM of VX809 (Selleck) for 48 hours. The assay was repeated as described above in the presence and absence of 7 uM CFTR inhibitor-172 (Sigma-Aldrich) to confirm the specificity of the compound for CFTR. Intracellular fluorescence intensity was measured in 3 random areas from the wall of each organoid using ImageJ software and normalized over the minimum fluorescence value for each area. Error bars represent SD.

Cytochrome p450 Activity

Cyp3A4 activity was measured using the p450-Glo assay kit (Promega) according to the manufacturer's instructions and a P450-Glomax 96 microplate luminometer (Promega).

Timing of Experiments on CLC Organoids

Figure 3:
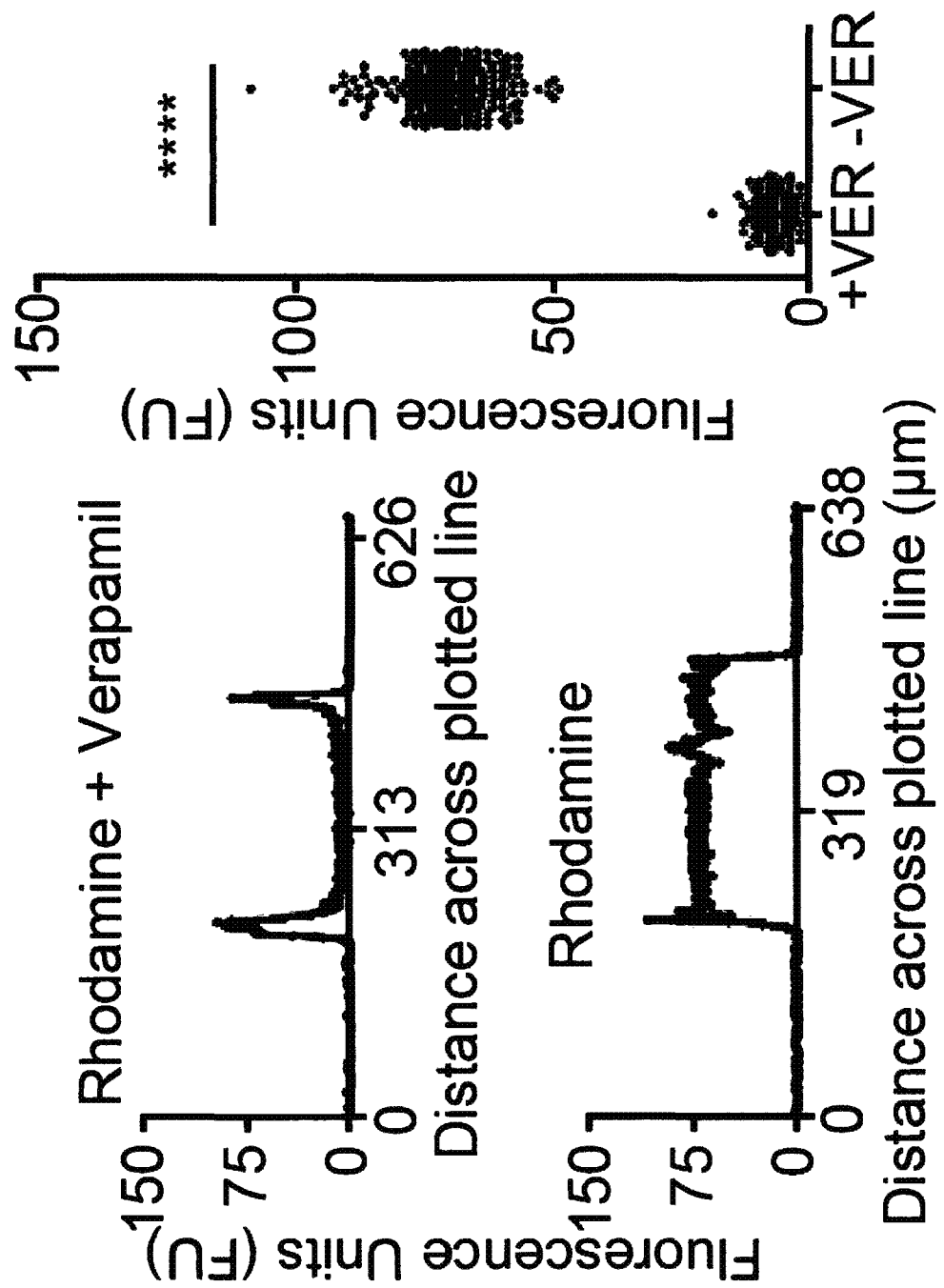
FIG. 3 shows (left) fluorescence intensity measurements from MDR1 fluorescent substrate Rhodamine123 across the lumen of CLC organoids and (right) the mean intra-luminal fluorescence intensity normalized over background, in the presence (+VER) or absence (−VER) of verapamil, n=599 measurements, $P=2.99 \times 10^{-5}$ (2-tailed t-test).

All the experiments and characterization with regards to CLCs were performed on CLC-organoids, following 10 days of 3D culture unless stated otherwise Statistical Analyses All statistical analyses were performed using GraphPad Prism 6 or the R statistical environment. For comparison between 2 mean values a 2-sided student's t-test was used to calculate statistical significance. For comparison between multiple values one-way ANOVA was used with Tuckey correction for multiple comparisons when comparing multiple values to each other (e.g. QPCR plots) or Dunnett correction for multiple comparisons when comparing multiple values to a single value (e.g. functional assays where the values are compared to a negative control). The normal distribution of our values was confirmed using the Kolmogorov-Smirnov test where appropriate. Further information on the statistical analysis of our data is provided in Supplementary table 7 (test used for each experiment/analysis, test statistic, degrees of freedom, P value). To smooth our data for generating the curves in FIG. 3g we used functional data analysis theory (50) implemented in the R package 'fda' (http://cran.rproject.org/web/packages/fdalindex.html).

First, we represented our data values (3 replications at each fluorescence intensity measurement) using 60 equidistant B-spline basis functions, and roughness penalties in the second derivative (lambda=1). We used the functions create.bspline.basis and smooth.fd in the interval 1-100 seconds. Then, we evaluated the mean and the standard deviation of the functional data objects using the R functions mean.fd and sd.fd.

Results

A Defined Culture System to Generate Cholangiocyte Progenitors from hIPSCs

Figure 2:
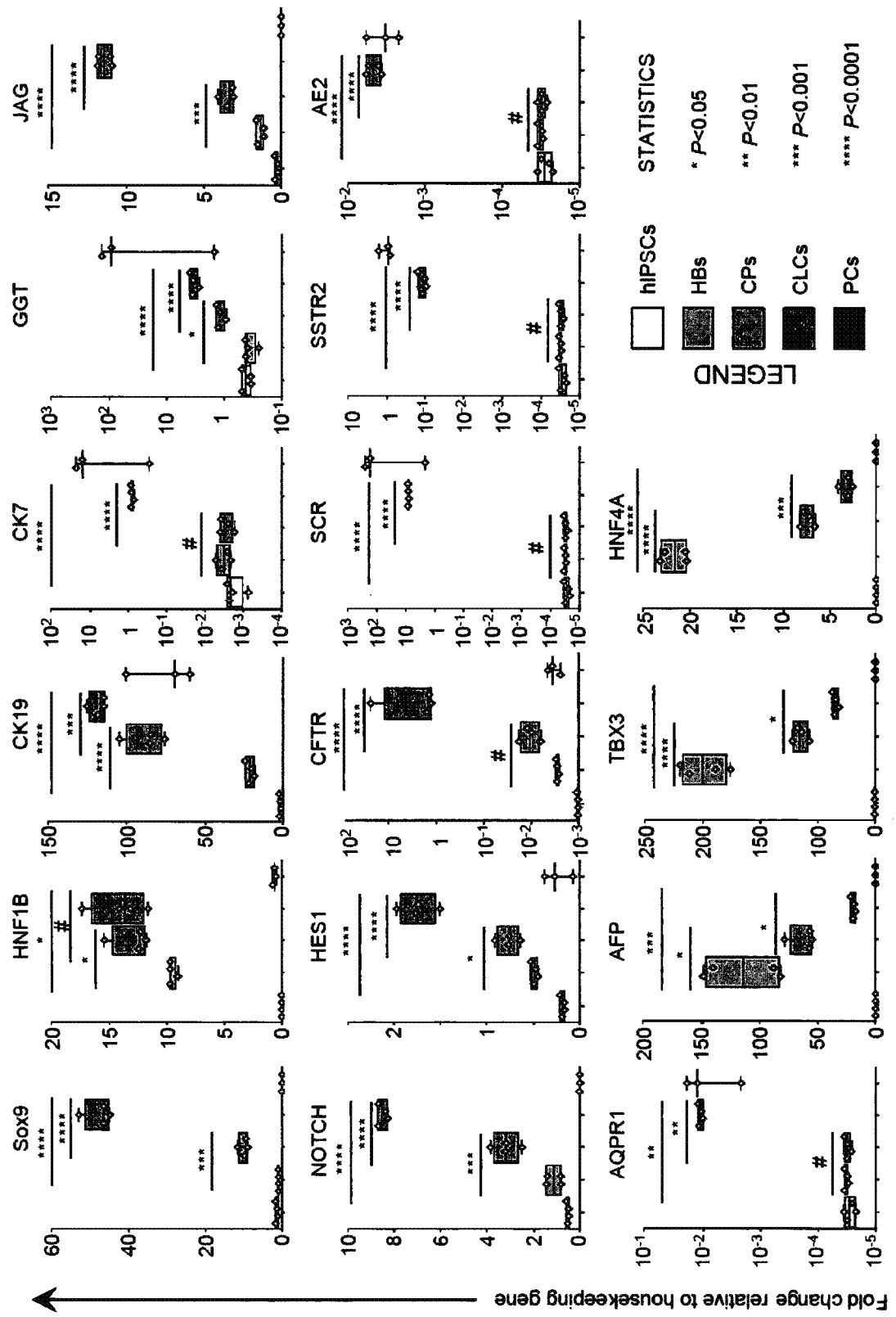
FIG. 2 shows the gene expression profile of hIPSC derived cells at key stages of biliary differentiation and primary cholangiocytes (PCs). n=4 biological replicates for each stage of differentiation. n=3 independent samples for PCs. Error bars represent standard deviation. Asterisks represent statistical significance of differences between HBs, CPs and CLCs (one-way ANOVA with Tuckey correction for multiple comparisons).

Our main objective was to generate a biliary differentiation platform recapitulating physiological bile duct development (6) (FIG. 1). To achieve this, we adapted our already established hepatic differentiation protocol (9-10). Cells generated with this methodology after 12 days of differentiation express a range of hepatoblast markers including AFP, HNF4A, HNF1B, TBX3, and CK19 (FIG. 2) and exhibit a potential to differentiate towards both the hepatic and biliary lineages (FIG. 2). Consequently, these cells represent a bipotent, hepatoblast-like population, providing an ideal starting point for our experiments. We then concentrated on the differentiation of hIPSC-derived hepatoblast-like cells into human Cholangiocyte Progenitors (CPs). We interrogated pathways reported to control early biliary specification (11) and demonstrated that Activin in combination with Retinoic Acid suppressed the expression of AFP, HNF4A and TBX3 while the addition of FGF10 induced the expression of SOX9, HNF1B and CK19 (FIG. 2), resulting in a near homogenous population of CK19+/Sox9+ cells with a differentiation efficiency of 75.1%. Flow cytometry analyses identified the majority of the remaining cells as Sox9−/AFP+ hepatoblasts, explaining the presence of reduced but detectable AFP levels in our culture. Mature biliary markers such as Secretin Receptor (SCR), Somatostatin Receptor 2 (SSTR2), Aquaporin1 and Anion Exchanger 2 (AE2) were not expressed (FIG. 2). Consequently, FGF10, RA and Activin promote the differentiation of hepatoblast-like cells into early cholangiocyte-like cells or cholangiocyte progenitors (CPs).

CPs Grown in 3D Culture Conditions Differentiate into Cholangiocyte-Like Cells

To further characterize hIPSC-derived CPs, we decided to use 3D culture conditions known to promote cholangiocyte maturation through organoid formation (6-8). CPs grown in these conditions proliferated rapidly, organized in ring like structures after 48-72 hours and within 5-7 days gave rise to cystic organoids and branching tubular structures, bearing primary cilia similar to those of primary cholangiocytes. Furthermore, the resulting organoids expressed a variety of mature biliary markers including CK7, CK18, CK19, HNF1B, Gamma Glutamyl-Transferase (GG7), Jagged1 (JAG1), NOTCH2, CFTR, SCR, SSTR2, Aquaporin and Anion Exchanger 2 (FIG. 2) at comparable levels with primary cholangiocytes (FIG. 2), providing indication that hIPSC-derived CLCs share key characteristics with their primary counterparts.

Figure 19:
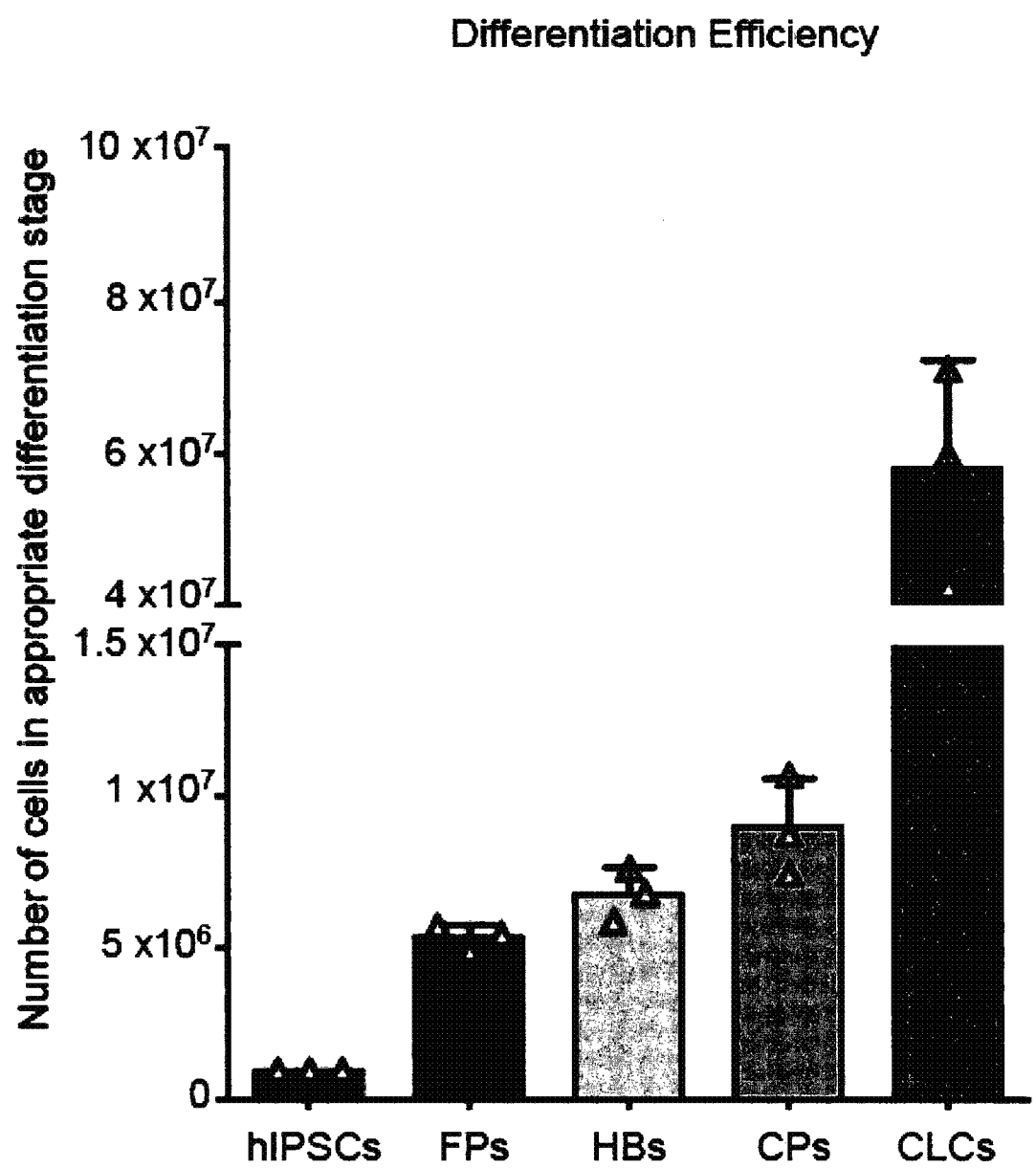
FIG. 19 shows the number of cells expressing appropriate markers for each key stage of CLC differentiation, demonstrating the generation of $57.8 \times 10^6$ mature (CK7+/Sox9+) CLCs from a starting population of $1 \times 10^6$ hIPSCs. Error bars represent SD, n=3.

We performed transcriptomic analyses interrogating Common Bile Duct (CDB) primary tissue and key stages of our differentiation protocol (Supplementary Table S2, FIG. 2e). Euclidian hierarchical clustering revealed that CLCs are transcriptionally distinct from earlier developmental stages and they cluster closely to primary common bile duct (CBD) cholangiocytes (Pearson correlation coefficient for CLCs vs. CBD r=0.747, CLCs vs. HBs r=0.576, CLCs vs. hIPSCs: r=0.474). Furthermore, CLCs express key mature (SSTR2, ALP, KRT7), but also fetal (SOX9) biliary markers, confirming previous QPCR analyses. Considered collectively these results confirm that CPs can differentiate into cells closely resembling biliary epithelial cells when grown in 3D culture. Importantly, we observed that starting from $1 \times 10^6$ hIPSCs, at the end of our differentiation protocol we generated $74.4 \times 10^8$ cells, of which $57.8 \times 10^6$ expressed mature biliary markers (FIG. 19). More specifically, 74.5% of the resulting cells co-expressed the biliary marker Sox9 and the mature biliary marker CK7, confirming the generation of near homogenous population of cholangiocytes. A further 7.5% of the cells expressed only Sox9 but not CK7, consistent with immature cholangiocytes. Of note, 15% of the cells co-expressed AFP and Albumin, indicating the presence of a small fraction of CPs or CLCs in our culture conditions and explaining the detection of low AFP levels on QPCR analyses (FIG. 2). The remaining 3% of the cells were not characterized further. These results were confirmed on 3 independent hIPSCs lines. Overall, these observations demonstrate that our system allows the production of large quantity of CLCs with the efficacy required for large scale applications.

Figure 4:
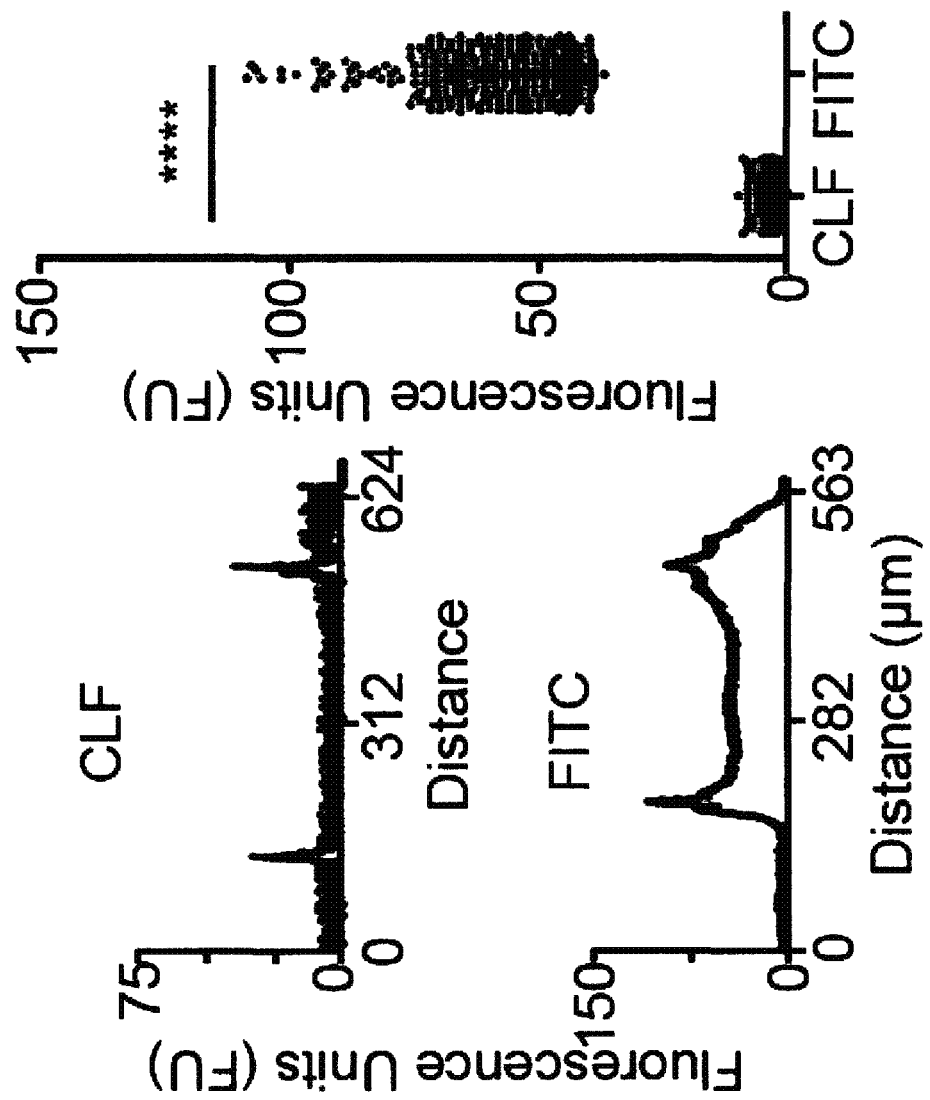
FIG. 4 shows (left) fluorescence intensity measurements from fluorescent bile acid cholyl-lysyl-fluorescein (CLF) across the lumen of CLC organoids and (right) the mean intra-luminal fluorescence intensity normalized over background n=1163 measurements, $P<1 \times 10^{-18}$ (2-tailed t-test). The data shown is representative of 3 different experiments.
Figure 5:
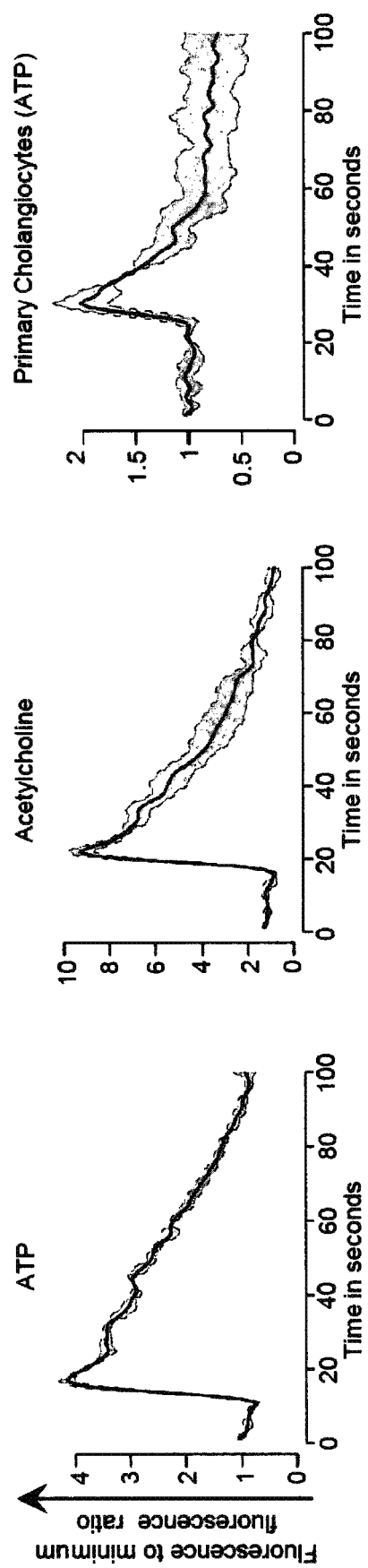
FIG. 5 shows fluorescence intensity measurements of CLC organoids loaded with the calcium indicator Fluo-4, demonstrating an increase in intracellular calcium levels following stimulation with ATP and acetylcholine. Plated primary cholangiocytes stimulated with ATP are used as a positive control. Grey area represents 1 SD, n=3.
Figure 6:
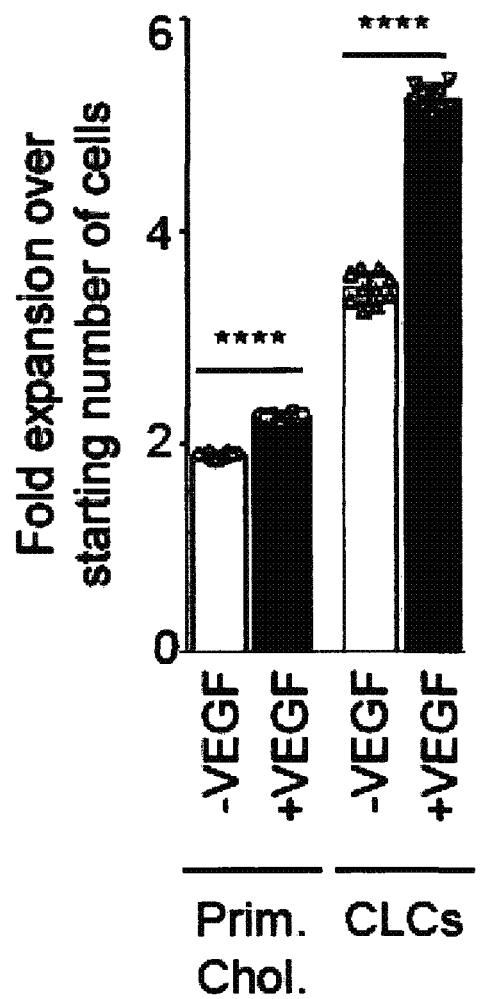
FIG. 6 shows the fold change over-starting number of cells in the presence and absence of VEGF for 5 days, demonstrating that VEGF promotes CLC proliferation. Prim. Chol. Plated primary cholangiocytes, n=10, $p=4.77 \times 10^{-17}$ (CLCs), $p=4.63 \times 10^{-17}$ (Prim. Chol.) (2-tailed t-test).
Figure 7:
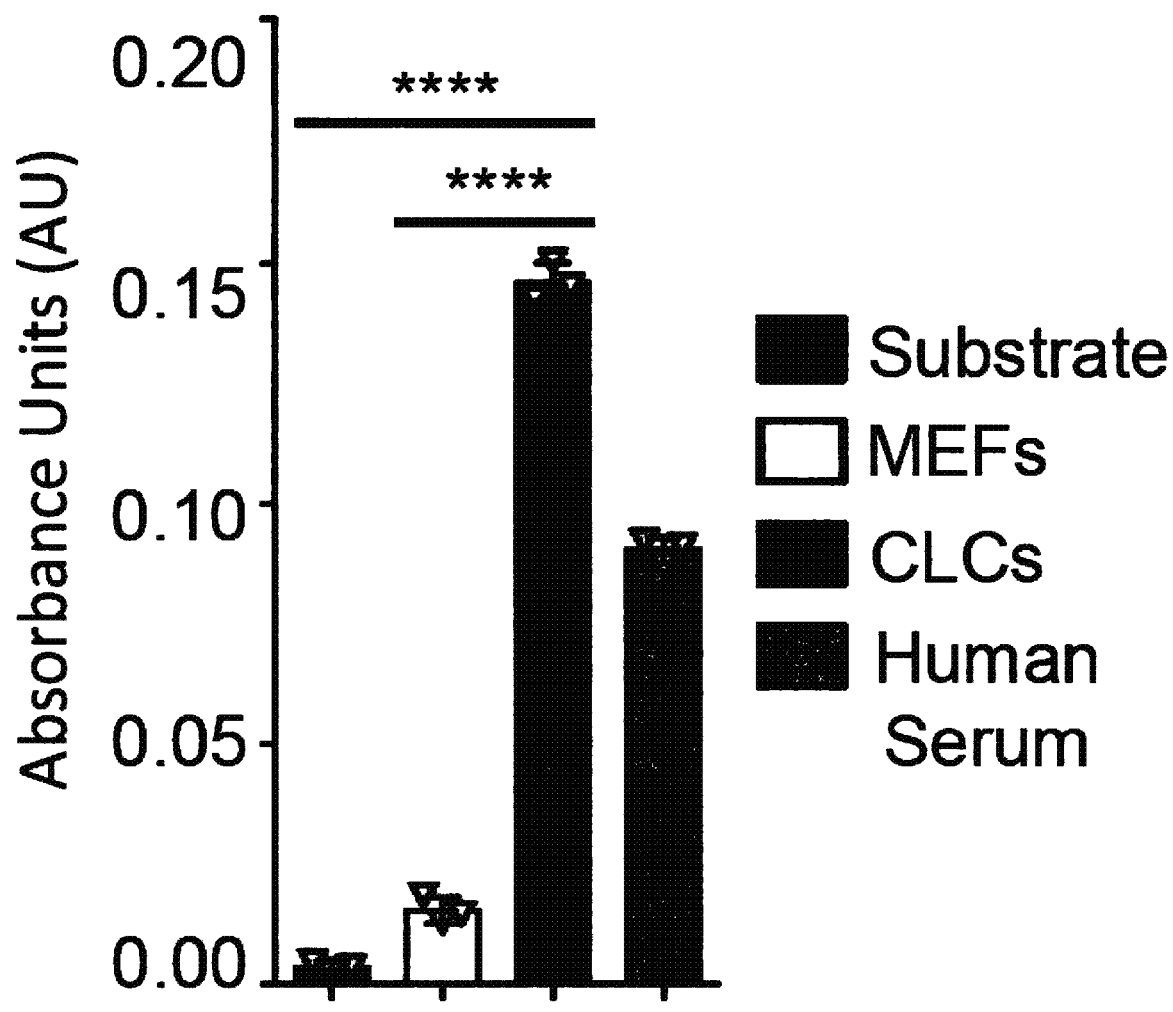
FIG. 7 shows the GGT activity exhibited by CLC organoids MEF: Mouse Embryonic Feeders, n=3, p<0.0001 for all comparisons (one-way ANOVA with Dunnett correction for multiple comparisons).

Having established the expression of appropriate biliary markers by cholangiocyte-like cells, we focused on characterizing the functionality of the generated organoids. In vivo, cholangiocytes re-absorb bile acids (12) and modify the composition of canalicular bile through a series of secretory and re-absorptive processes (13) regulated by intracellular calcium signaling (14). Furthermore, native biliary epithelial cells express Alkaline Phosphatase (ALP) and GGT activity and proliferate in response to stimuli such as Vascular Endothelial Growth Factor (VEGF). The secretory potential of cholangiocyte like cells generated in vitro was confirmed using Rhodamine123, a fluorescent substrate for the cholangiocyte surface glycoprotein Multidrug Resistance protein-1 (MDR1) (15, 16). Rhodamine123 was actively secreted in the lumen of CLC organoids; however, luminal dye accumulation was prevented by the MDR1 inhibitor verapamil (FIG. 3), confirming MDR1-dependent transfer of Rhodamine123. The capacity of cholangiocyte-like cells for interacting with bile acids through the Apical Salt and Bile Transporter (ASBT)(12) was also demonstrated by showing active export of the fluorescent bile acid Cholyl-Lysyl-Fluorescein (CLF) from the lumen of CLF loaded organoids compared to controls loaded with Fluorescein Isothiocyanate (FITC) (FIG. 4). ASBT expression was confirmed through QPCR and IF analyse. Additional aspects of cholangiocyte-like cell secretory functions, including CFTR activity and response to secretin and somatostatin stimulation were also validated (See below). Furthermore, cholangiocyte-like cells responded to acetylcholine and ATP stimuli by increasing intracellular calcium levels (FIG. 5), demonstrated increased proliferation in response to VEGF stimulation (51% increase in fold expansion, P<0.0001, 2-tailed t test) (FIG. 6) and exhibited GGT and ALP activity comparable to primary controls (GGT activity: 160% of human serum, P<0.0001, one-way ANOVA with Dunnett correction for multiple comparisons) (FIG. 7). Considered collectively, these observations confirm that hIPSC-derived CPs can give rise to cholangiocyte-like cells displaying a range of functions specific to the native biliary epithelium. Differentiation of hIPSCs into Cholangiocyte-Like Cells Represents a Novel Model to Study the Embryonic Development of the Human Biliary System.

Figure 8:
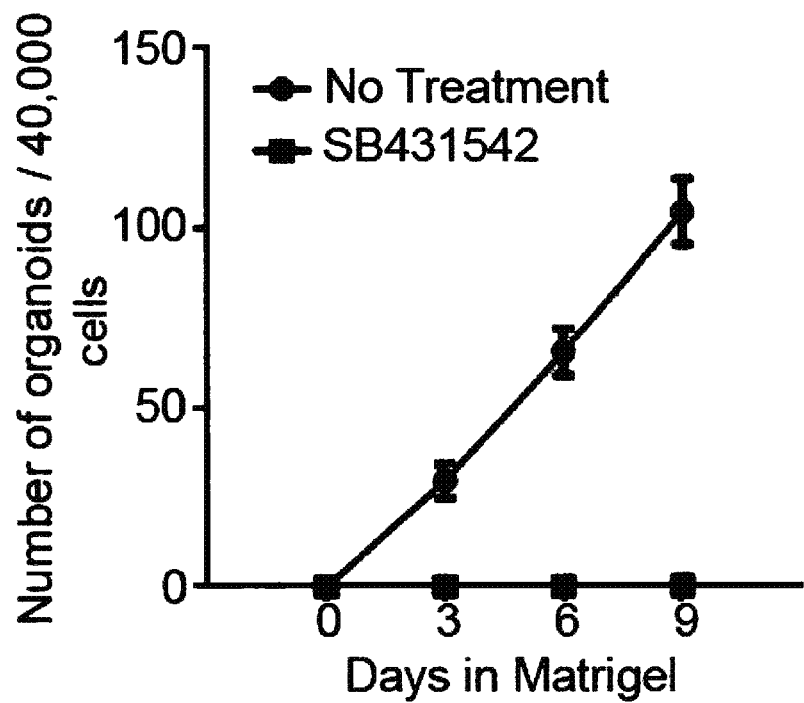
FIG. 8 shows the number of CLC organoids following culture of CPs in matrigel in the presence and absence of SB-431542, demonstrating suppression of organoid formation secondary to inhibition of activin signaling. Error bars represent SD, n=4.

To investigate potential applications of our system for developmental studies, we characterized signaling pathways controlling organoid formation in vitro and how they compare with native duct development. First, we interrogated Activin/TGFβ signaling in view of its pivotal role in physiological biliary specification and tubulogenesis (11, 17, 18). To achieve this, we blocked the activity of TGFβ, which is normally contained in Matrigel using the Activin receptor inhibitor SB-431542. SB-431542 completely negated organoid formation (FIG. 8) confirming the role of Activin/TGFβ signalling as a key regulator of organoid formation in our system.

Figure 9:
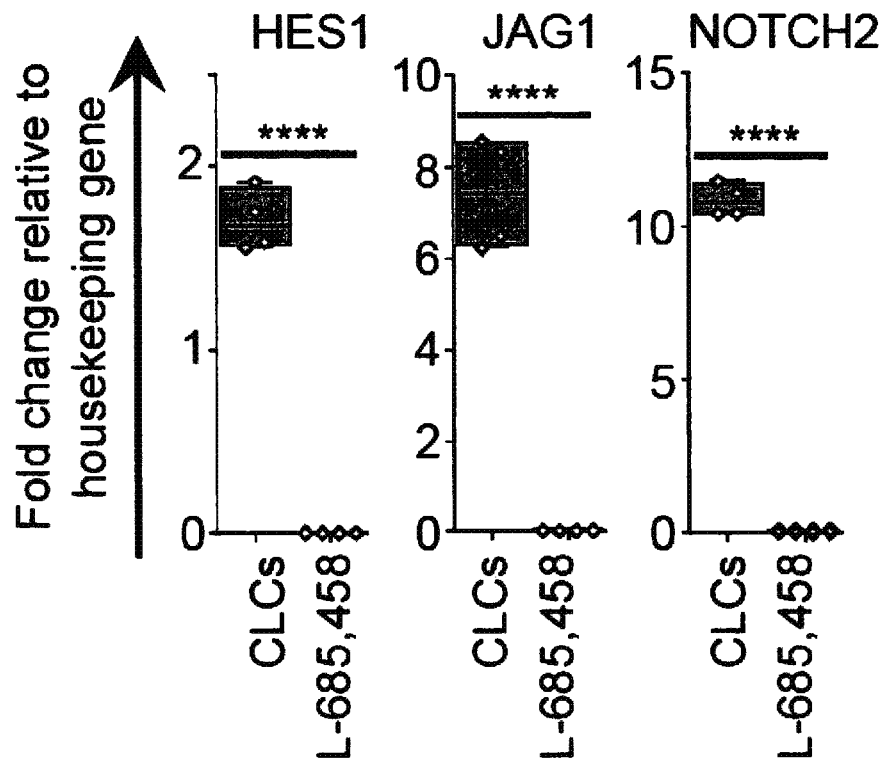
FIG. 9 shows QPCR analyses for the expression JAG1, NOTCH2, and the Notch downstream target HES1 in CLC organoids vs. CP cultured in matrigel in the presence of L-685,458, demonstrating reduced expression of this marker in response to L-685,458, n=4. Error bars represent SD. ***P<0.0001 (two-tailed t-test).
Figure 10:
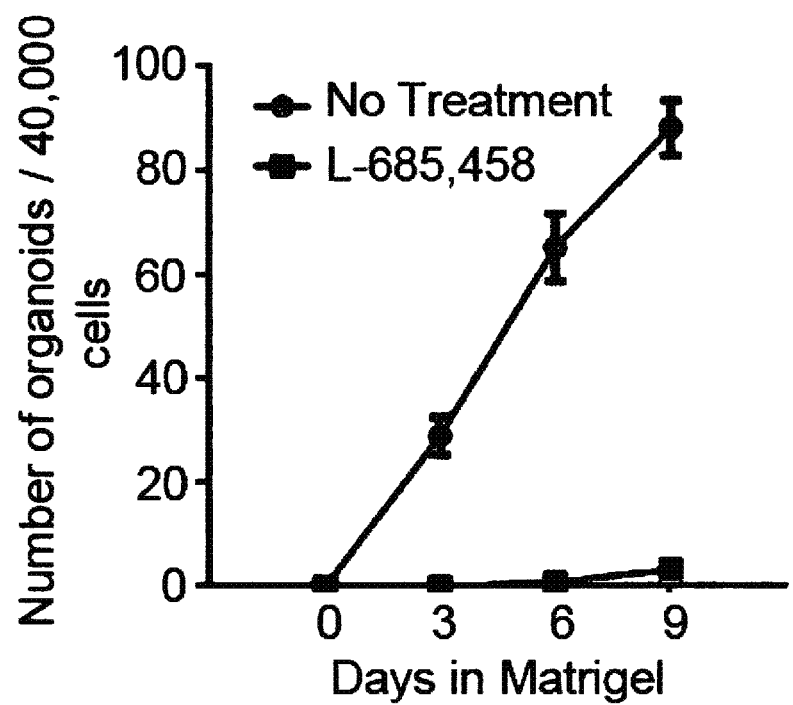
FIG. 10 shows the number of CLC organoids following culture of CPs in matrigel in the presence and absence of L-685,458 demonstrating a significant reduction in organoid formation, following inhibition of Notch signaling. Error bars represent SD, n=4.

Similar analyses were performed with Notch signalling, the deregulation of which is associated with Alagille Syndrome (AGS), a disorder characterized by paucity of bile ducts (19). To study the role of Notch signaling, we first assessed the activity of this pathway during biliary specification of hepatoblasts to CPs and organoid formation in vitro. Notch activation results in cleavage of its intracellular domain and nuclear translocation (20, 21). Immunofluorescence (IF) with antibodies against the active (cleaved) form of the Notch Intracellular Domain (NICD) confirmed the presence of active NICD, with increased nuclear localization in CPs and CLC organoids. The expression of NOTCH2, as well as its ligand JAG1 and its downstream target HES1 were also increased in both stages compared to hepatoblasts, in keeping with pathway activation (CPs vs. HBs: NOTCH2: P<0.001, JAG1: P<0.001, HES1: P<0.05; CLCs vs. CPs or HBs: P<0.0001) (FIG. 2). Inhibition of Notch signaling in 3D culture conditions using the gamma-secretase inhibitor L-685,458 blocked cleavage of the NICD, suppressed HES1, NOTCH2 and JAG1 expression (FIG. 9) and blocked organoid formation (FIG. 10), thereby confirming the importance of Notch signaling for the generation of organoids incorporating a luminal space in our system. Considered collectively, these results reinforce previous findings obtained in mice by demonstrating the importance of these signalling pathways in human cholangiocyte specification (22) and underline the potential of our culture system for modelling and studying human biliary tree development in vitro.

hIPSC-Derived CLCs Allow Drug Validation for Polycystic Disorders of the Liver

Figure 11:
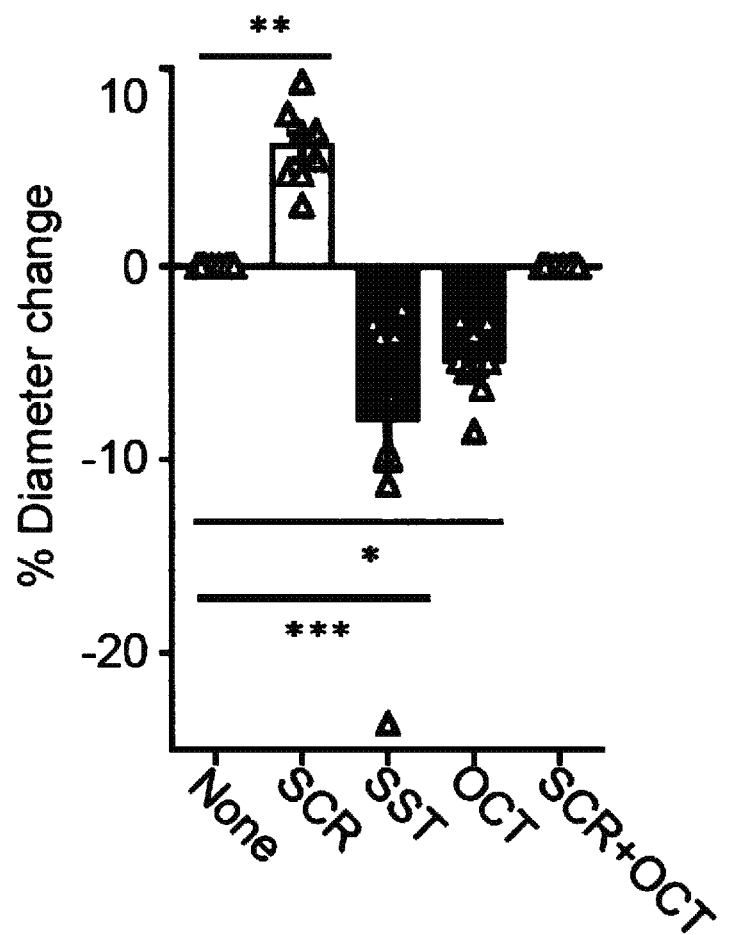
FIG. 11 shows the effect of secretin (SC), somatostatin (SST), octreotide (OCT) and the combination of secretin and octeotide on CLC organoid diameter. Error bars represent SEM, n=8, *P<0.05, P<0.01, *P<0.001, ****P<0.0001 (one-way ANOVA with Dunnett correction for multiple comparisons.
Figure 12:
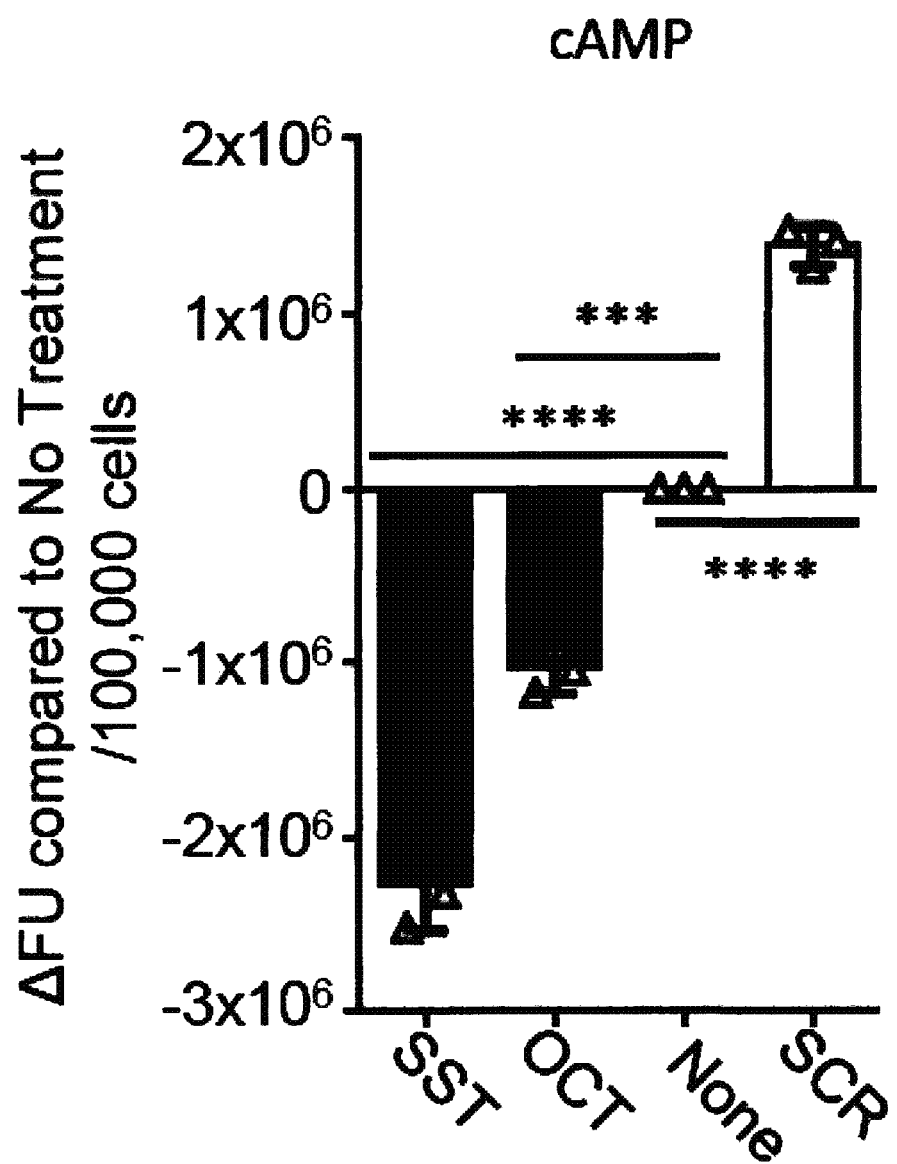
FIG. 12 shows that secretin treatment increases, while somatostatin and octreotide treatment decrease cAMP levels in CLC organoids. Error bars represent SEM, n=3, Asterisks represent statistically significant differences (one-way ANOVA with Dunnett correction for multiple comparisons).
Figure 13:
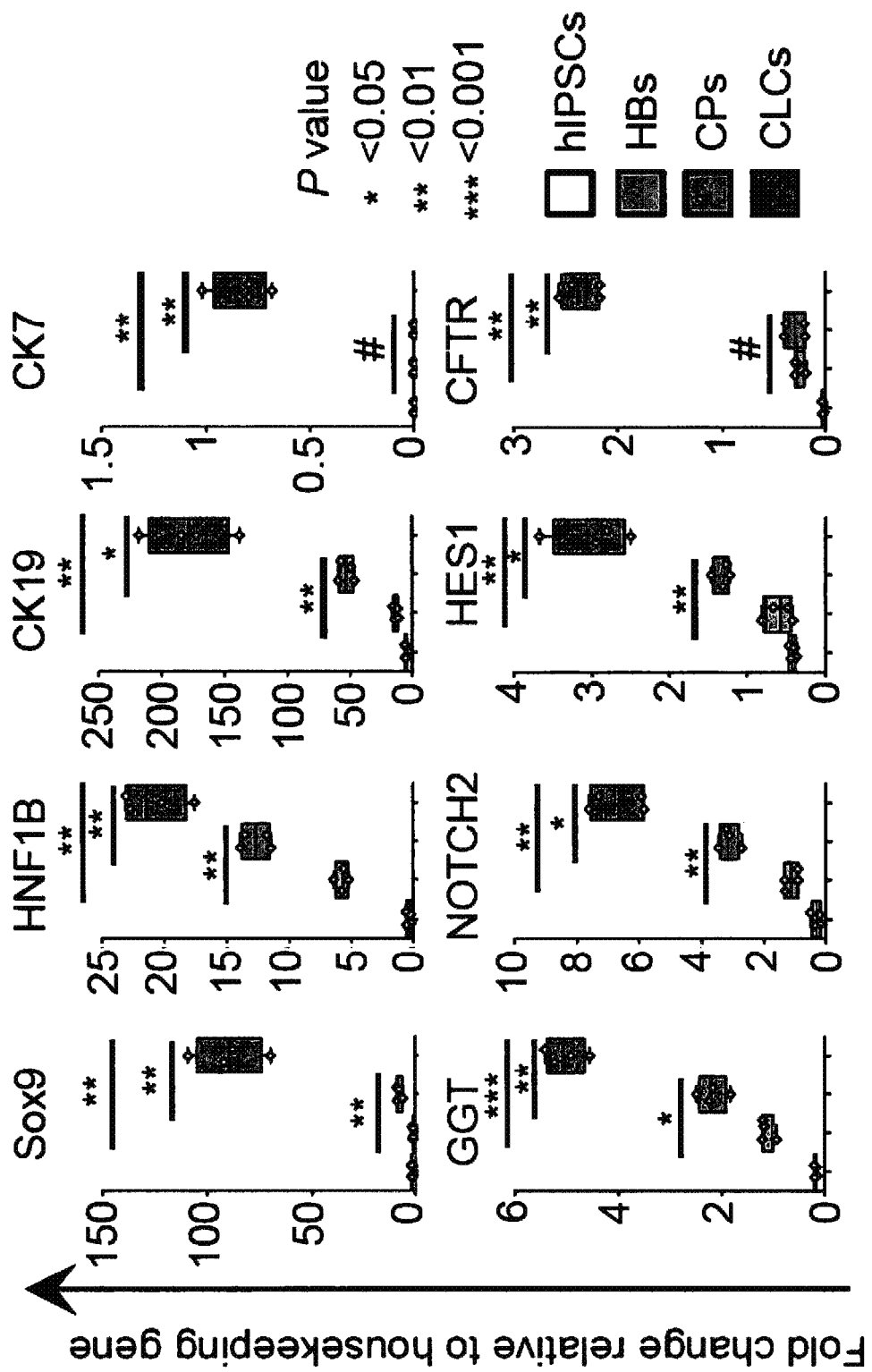
FIG. 13 shows QPCR demonstrating the expression of biliary markers in PLD-CLCs. Asterisks represent statistical significance in differences between HBs, CPs and CLCs (one-way ANOVA with Tuckey correction for multiple comparisons).
Figure 14:
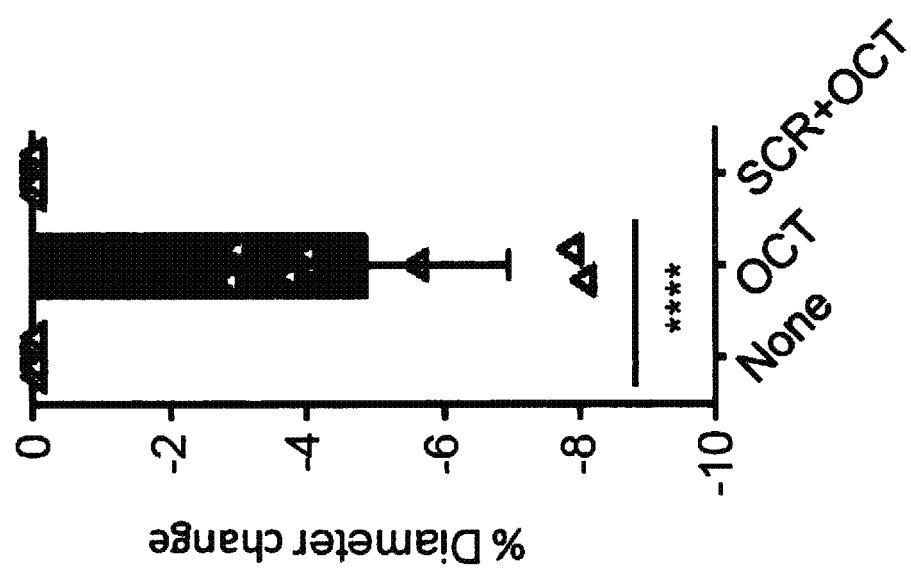
FIG. 14 shows diameter measurements in PLD-CLC organoids pre and post treatment with octreotide or the combination of secretin and octreotide, ****: P<0.0001 (one-way ANOVA with Dunnett correction for multiple comparisons). The data shown is representative of 3 different experiments.

Polycystic liver diseases (PLDs) are characterized by the presence of multiple cystic lesions in the liver arising from fetal cholangiocytes (23-24). We decided to explore the potential of hIPSC derived CLC organoids for screening compounds reducing cyst size in PLD. Physiologically, cholangiocyte secretory activity is increased by secretin and reduced by somatostatin and its synthetic analogue octreotide, resulting in respective changes in duct size (26-29). Cholangiocyte-like cell organoids express both secretin (SCR) and Somatostatin Receptor 2 (SSTR2) (FIG. 2) suggesting that these pathways could be functional in our cells. Accordingly, secretin increased (6.1% average diameter increase, P<0.01, one-way ANOVA with Dunnett correction for multiple comparisons) while somatostatin and octreotide decreased organoid size, compared to untreated controls (7.9% and 4.9% average diameter decrease respectively, p<0.001 and p<0.05 respectively, one-way ANOVA with Dunnett correction for multiple comparisons) (FIG. 11). Furthermore, octreotide negated the effects of secretin and decreased intracellular cAMP levels (45% of somatostatin response, P=0.001, one-way ANOVA with Dunnett correction for multiple comparisons) in keeping with previous studies (26, 30) (FIG. 12). To further test the effects of octreotide on disease-specific CLCs, hIPSCs derived from a patient with Polycystic Liver Disease (PLD), were differentiated to PLD-CLCs (FIG. 13). Octreotide treatment reduced PLD organoid size (4.86%, P<0.0001, one-way ANOVA with Dunnett correction for multiple comparisons) (FIG. 14), reproducing the effects of the drug in vitro. Considered collectively, these observations demonstrate that hIPSC-derived cholangiocyte organoids respond to physiological secretory stimuli and provide proof of principle that our in vitro differentiation platform can be used to screen drugs affecting duct size in the context of PLD.

Modeling Cystic Fibrosis Liver Disease Using hIPSC-Derived CLC

Figure 15:
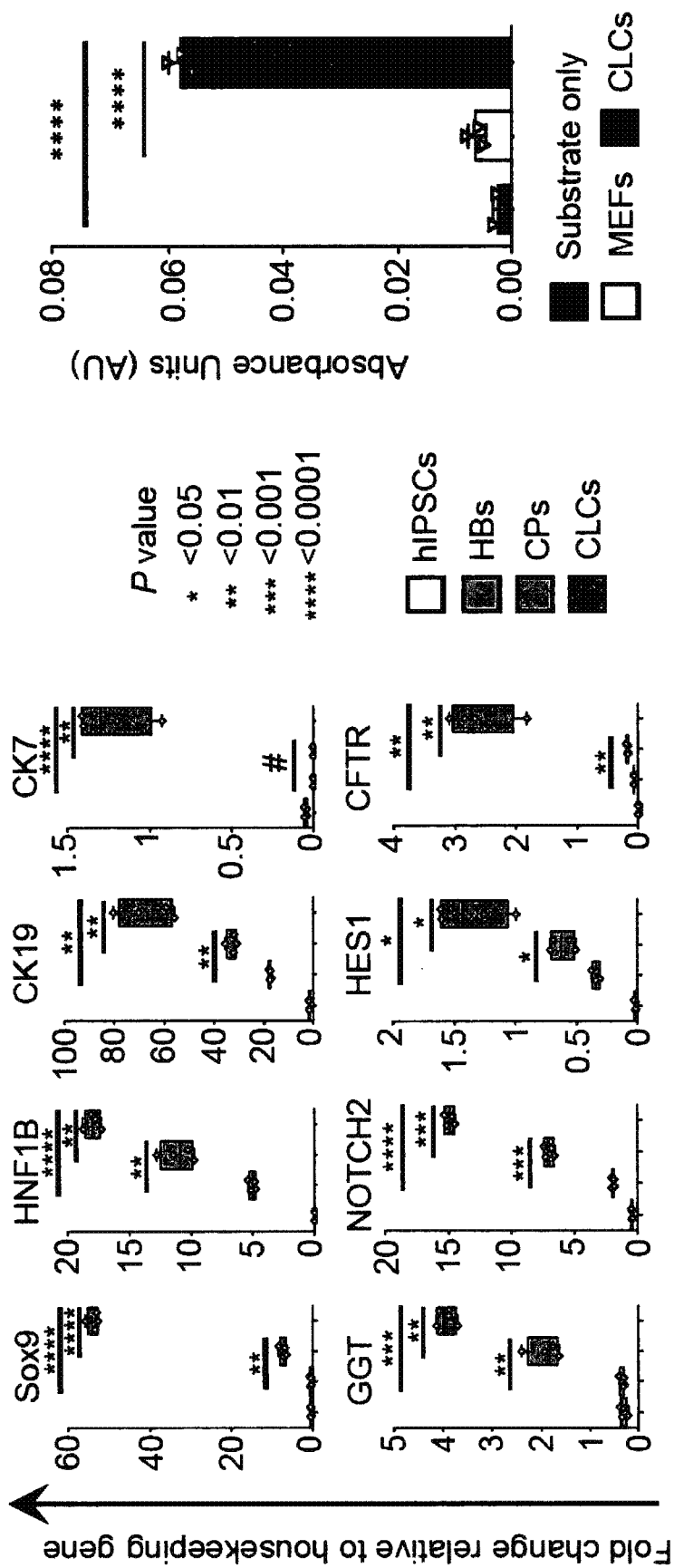
FIG. 15 shows modeling Cystic Fibrosis (CF) liver disease in vitro, using hIPSCs derived from patients with CF. Left panel shows QPCR analyses of CLC organoids generated from CF-hIPSCs (CF-CLC), demonstrating the expression of biliary markers. Asterisks denote statistical significance in differences between HBs, CPs and CLCs (one-way ANOVA with Tuckey correction for multiple comparisons). Right panel shows CF-CLC organoids exhibit GGT activity. ****: P<0.0001 (one-way ANOVA with Dunnett correction for multiple comparisons).
Figure 16:
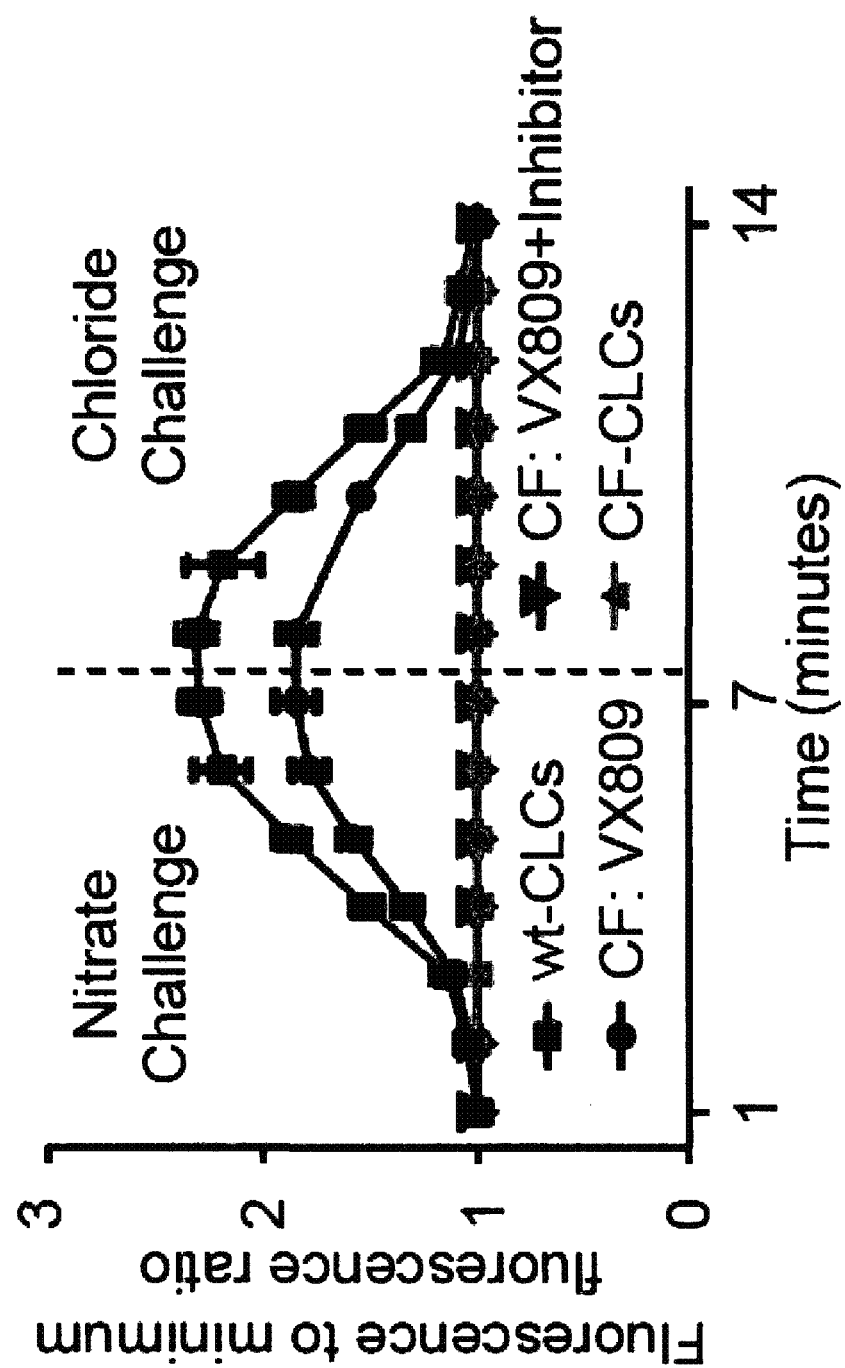
FIG. 16 shows MQAE fluorescence intensity normalized over the lowest intensity value. MQAE fluorescence is quenched in the presence of chloride, but not affected by nitrate. Changes in intracellular or intra-luminal chloride levels in response to extracellular chloride levels depend on the presence of CFTR functionality. MQAE fluorescence increases in response to a nitrate challenge depleting extracellular chloride and decreases in response to chloride in wt- and CF-CLCs treated with VX809, however fails to respond to both challenges in CF-CLCs and CF-CLCs treated with VX809+CFTR inhibitor-172.
Figure 17:
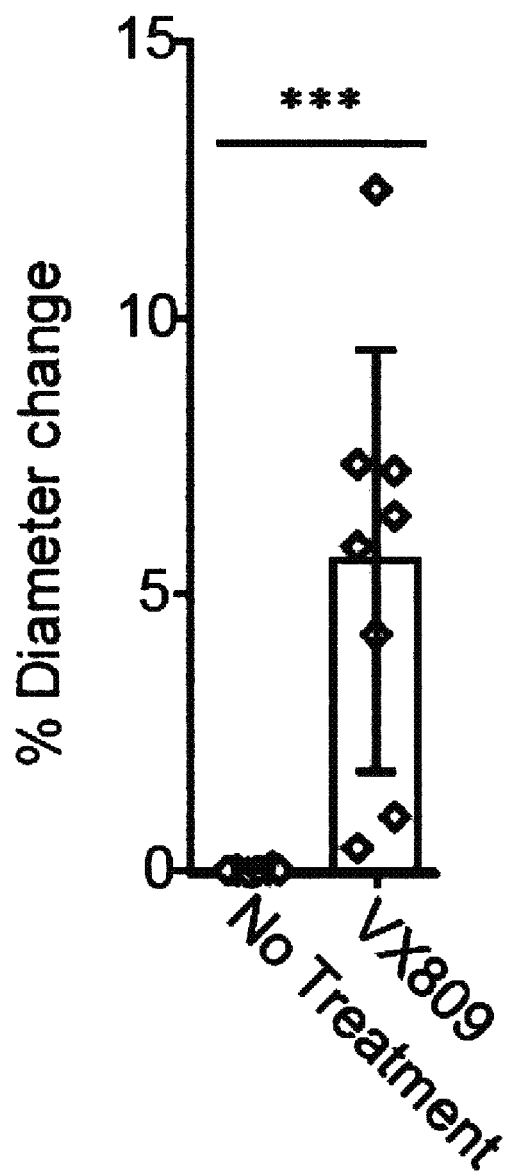
FIG. 17 shows the effect of VX809 treatment on mean organoid diameter. Error bars represent SD, n=8, P=0.001, (2-tailed t-test). Images cropped to include 1 cyst, but representative. All data shown is representative of 3 different experiments.

To further explore clinical applications of our culture system, we decided to model biliary disease in vitro using hIPSCs derived from a patient with Cystic Fibrosis (CF). hIPSCs were generated from skin fibroblasts of a patient homozygous for the most common CF mutation ΔF508 (CF-hIPSC) and then differentiated into cholangiocyte-like cells. CF-hIPSC derived Cholangiocyte-Like Cells (or CF-CLCs) expressed markers (FIG. 15) and displayed functionality characteristic of biliary epithelial cells (FIG. 15). Transcription of the CFTR gene was confirmed using QPCR (FIG. 15), while IF analyses detected minimal CFTR protein expression in agreement with studies reporting very rapid ER degradation of the misfolded protein (35). Finally, we used the fluorescent chloride indicator N-(6-methoxyquinolyl)acetoethyl ester (MQAE) (36) to monitor intracellular and intraluminal chloride concentration, which is physiologically regulated through CFTR. Wild type (WT) CLC organoids appropriately modified intracellular chloride in response to media with varying chloride concentrations while no change was observed in CF-CLCs (FIG. 16) thereby confirming the absence of functional CFRT in these cells. Overall, these results demonstrate that CF-CLCs recapitulate key aspects of CF in vitro and thus provide a unique system to model the biliary disease induced by CF. Having reproduced the phenotype of CF liver disease in vitro, we decided to investigate the efficacy of VX809 for rescuing the disease phenotype in the context of biliary disease. Currently, the treatment for CF liver disease is symptomatic (37). However, new compounds stabilizing CFTR and correcting folding defects in patients with the ΔF508 mutation have recently been developed to treat lung symptoms. VX809 is such a compound (38), reported to increase CFTR functionality in lung cells (39). CF-CLCs were grown for 48 hours with VX809 and then CFTR function was analyzed using MQAE. The resulting cells exhibited increased CFTR functionality, comparable to WT CLCs establishing the efficacy of VX809 on biliary cells. This effect was negated in the presence of CFTR inhibitor-172, confirming that the phenotype rescue of CF-CLCs by VX809 was indeed secondary to increased CFTR functionality (FIG. 16). In view of the association between chloride and fluid secretion in cholangiocytes (31), we investigated the impact of VX809 on organoid size. CF-CLC organoids treated with VX809 demonstrated an increase in size compared to their untreated counterparts (5.6% mean 23 diameter increase, P=0.001, 2-tailed t-test) (FIG. 17). These observations confirm that VX809 increases CFTR function and improves intraluminal fluid secretion, thus suggesting a previously unreported therapeutic effect for this drug in the context of CF liver disease. Considered collectively, these results demonstrate the potential of CLC organoids for modelling biliary disorders in vitro and support a novel role for VX809 in the management of CF-associated cholangiopathy.

Comparison of CLCs with Cells from Existing Protocols

Previous reports have suggested that generation of cholangiocytes from human PSCs could be feasible (6-8). Of particular interest, the cells generated by Dianat and colleagues have been the best characterized so far (6). However, all these methods exhibit significant limitations and the cells generated through these systems lack expression of key biliary markers and functional properties. To better assess the advance of our platform over previous methods we performed a systematic comparison between CLCs and the cells generated by other protocols (Table 1) (6).

The Transcriptional Profile of CLCs Exhibits Greater Overlap with Primary Cholangiocytes First, we decided to compare the gene expression profile of our CLCs to those generated by Dianat et al (6). (hECS-Chol), both at the gene and probe set level, using our microarray data and their data uploaded in GEO. We observed a more similar transcriptional signature between cholangiocyte-like cells generated with our protocol and primary bile duct tissue (median of the Spearman rank-based correlations of the z-scores across replicates, $\rho CLC=0.86$; n=14939) than hESC-derived cholangiocytes generated by Dianat et al. ($\rho hESC-Chol=0.51$). Hierarchical cluster analysis (Euclidean distance, complete linkage method) of normalized samples and mutual information (MI), an entropy measure of nonlinear distance between the expression profiles, confirmed this result (MICLC=0.62 and MIhESC-Chol=0.54, median across replicates; see Suppl. Methods). These results show that our CLCs are more similar to primary bile duct cholangiocytes compared to the cells generated by others (6).

Analogous analyses repeated at the common gene set reference instead of probes shed light on same conclusions ($\rho'CLC=0.83$; $\rho'hESC-Chol=0.62$; MI'CLC=0.80; MI'hESC-Chol=0.73; n=15954). Results using more than one metric (Spearman correlation and mutual information) to measure the similarities between the datasets, both between genes and probes, were all in agreement, with our cells outperforming in the comparison.

Furthermore, the expression of 21 cholangiocyte-specific genes of key biliary markers ranked at higher levels in our CLCs compared to the alternative protocol, including SOX9, HNF1B, HNF6, NOTCH, HES1, GGT, ALP, CFTR, ASBT (Table 2).

In addition to similarity metrics on gene expression values, we have performed Percentage of Overlapping Function (POF) analyses to assess the similarity of the most highly expressed genes between samples at the functional level (4) based on overlapping Gene Ontology (GO) terms (biological processes). Functional comparisons of the microarray datasets across the multiple platforms using POF analysis revealed higher similarity between ranked significantly enriched GO terms (p<0.05, Bonferroni adjustment) of most highly expressed genes between CLCs and the primary controls (mean POF 71.82% for CLCs, 66.08% for hESC-Chols, 62.94% for hepatoblast (HBs), 53.64% for hPSCs). Collectively, these results prove that our protocol allows the generation of cholangiocyte-like cells which more closely resemble their in vivo counterparts when compared to cells obtained by alternative protocols (6).

CLCs Exhibit a Unique Panel of Enhanced Functions Characterizing Cholangiocytes

The majority of the functional properties demonstrated for CLCs in the current study have not been reported in previous protocols, preventing a direct comparison. These include ALP, GGT (FIG. 7) and CFTR activity (FIG. 16), response to secretin (96%) (FIG. 11) and VEGF (FIG. 6). To overcome this limitation we compared the expression of the enzymes, receptors or membrane proteins controlling these functions using our microarray data and the data uploaded in GEO by Dianat et al. (6). Our comparison reveals that relevant genes such as ALP, GGT, CFTR, SCTR, SSTR2 are expressed at lower levels in cells generated by Dianat et al (Table 2), which provides an explanation as to why the functional properties demonstrated in CLCs have never been previously reported.

Figure 18:
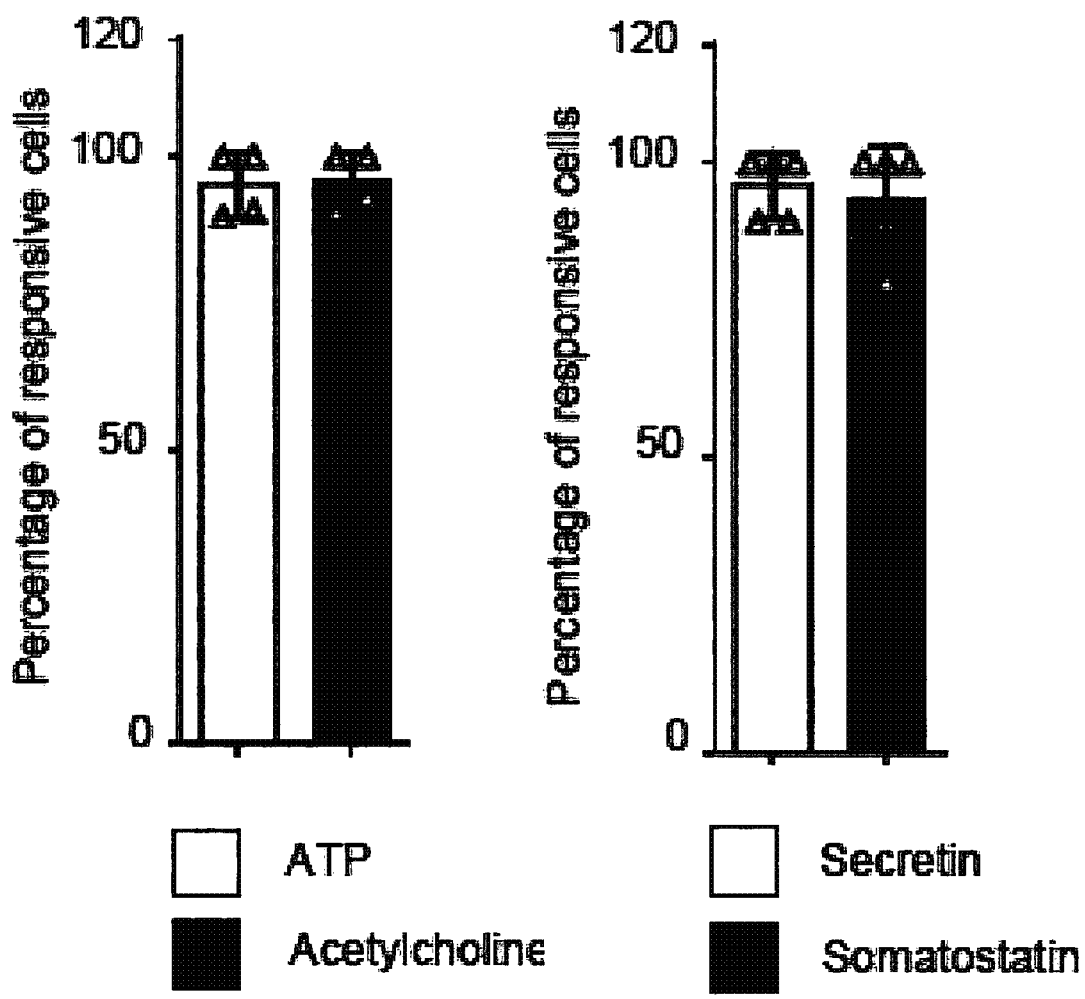
FIG. 18 shows (right) the percentage of CLCs responding to calcium stimulation through ATP or acetylcholine, n=4. Error bars represent SD and (left) the percentage of CLC organoids responding to secretin or somatostatin stimulation, n=4. Error bars represent SD.

Furthermore, we directly compared shared functional characteristics between both cell types. Somatostatin treatment induced a reduction in size (diameter) in 94% (FIG. 18) of the CLC organoids vs. a 31% response in hESC-Chol. (6). Responsiveness to ATP and acetylcholine was calculated at 95% and 96% respectively in CLCs (FIG. 18) vs. 70% and 40% respectively in hESC-Chol. Importantly, we have demonstrated the capacity of CLCs to transfer fluorescent bile acids, extruding them from the organoid lumen (FIG. 4). The transfer of bile acids (BAs) has also been described by Dianat et al (6); however, hESC-Chol exhibit a paradoxical response, accumulating BAs in the organoid lumen rather than extruding them (5-7). This observation could be explained by the presence of a significant contaminating hepatoblast population, which is known to secrete BAs in the canalicular space (8). Considered collectively, these data confirm that CLCs generated by our protocol constitute a significant advance in the field in terms of functionality and expression of key functional markers.

Enhanced Differentiation Efficiency and Capacity for Large Scale Applications.

The efficiency of our differentiation methodology is 75% for the generation of mature CK7+/Sox9+ CLCs with >94% functional cells (based on secretin, somatostatin, ATP and acetylcholine responsiveness. Similar analyses were not performed in any previous studies. Only Dianat et al. (6) have characterized their population of cells using flow cytometry analyses for the expression of (CFTR) which unfortunately lacks specificity for biliary tissue (9). Due to this limited characterization, homogeneity of differentiation is difficult to precisely assess, but could at best be 31% based on SST responsiveness (6). Furthermore, our system exhibits a 57-fold expansion capacity for the generation of mature CLCs (FIG. 19). None of the other studies report such capacity for cell expansion suggesting limitations in differentiation efficiency. Thus, our protocol constitutes a significant improvement in terms of differentiation efficiency and homogeneity of the resulting population, with a unique capacity for large scale applications not demonstrated previously.

The Generation of Cholangiocyte Progenitors Under Chemically Defined Conditions Enables Developmental Studies Previous protocols either rely on spontaneous differentiation (7,8), undefined products such as serum (6) and/or growth factors which have not been reported to enhance biliary differentiation in vivo (GH, IL6, Sodium taurocholate) (6), posing a significant challenge for developmental studies focused on the identification of pathways driving cholangiocyte specification. On the contrary, up to and including the differentiation of hepatoblasts to cholangiocyte progenitors, our system relies on chemically defined conditions and factors shown to promote biliary specification in vivo (FGF10 and activin) (18,40), allowing the generation a highly homogeneous population of early cholangiocyte progenitors (75% CK19+/Sox9+ cells), which has never been previously reported.

Furthermore, the formation of biliary organoids in our culture system is controlled by pathways reported to instruct biliary tubulogenesis in vivo, such as Notch signaling, which has been associated with AGS, a disorder of bile duct development (19, 22). A similar requirement for Notch signaling has not been demonstrated previously. This could be due to limited pathway activity, evidenced by lower expression of Notch and its downstream target HES1 in previous systems (6) (Table 2). Together, these observations illustrate the enhanced potential of our culture system for studying basic mechanisms controlling biliary development and the pathogenesis of developmental bile duct disorders, such as AGS.

CLCs Provide the First hIPSC-Based Platform for Disease Modeling and Drug Screening Medical and pharmaceutical applications of hIPSCs in the context of biliary disorders, such as disease modeling and drug screening have never been previously reported. To examine the potential of the cells generated by Dianat et al. (6) for such applications, we directly compared the expression of the key genes involved in the pathogenesis of cholangiopathies or mediating the effects of pharmaceutical compounds on cholangiocytes between CLCs and hESC-Chol. These include CFTR (involved in the pathogenesis of CF and mediating the effects of VX809), PKD (Polycystic Liver and Kidney Disease), NOTCH and HES1 (AGS), SSTR2 (mediating the effects of octreotide) (Table 2). Our results demonstrate reduced expression of these key genes in hESC-Chol compared to CLCs, which could be explained by heterogeneity in cell population and/or a decrease in functional properties which play a critical role in the pathophysiology of cholangiopathies and the response to therapeutic agents (lack of CFTR activity, no requirement for Notch signaling, 30% response to SST). These data illustrate that our system provides a unique platform for multiple translational applications such as disease modeling and drug screening which would otherwise be unrealistic and unobtainable using chologangiocytes differentiated with other published protocols.

The development of an advanced platform for the generation of cholangiocyte-like cells from hIPSCs is described above. This platform demonstrates translational potential for drug screening and biliary disease modelling. Although methodologies for the derivation of cholangiocytes from stem cells have been described (6-8), these are significantly restricted by poor differentiation efficiency (31%) (6) and limited functionality of the resulting cells.

Our platform overcomes these challenges, generating a near homogeneous population of mature CLCs (75% CK7+/Sox9+ cells), with a transcriptional signature closely resembling primary bile duct tissue (Spearman correlation coefficient 0.830 s p s 0.833 vs. 0.614 s p s 0.622 with previous protocols (6)). Indeed, global gene expression analyses confirm that key biliary markers rank at higher levels in CLCs compared to cells generated through alternative platforms (6) including SOX9, HNF1B, HNF6, NOTCH, HES1, GGT, ALP. Functional assays further illustrate a considerable qualitative overlap between CLCs and native cholangiocytes in key functional properties, such as CFTR, ALP and GGT activity (160% of human serum values), bile acid transfer and responsiveness to VEGF, SCR (96%), SST (94%), acetylcholine (96%) and ATP (95%). Considered together, these data demonstrate that our differentiation platform advances the differentiation of hIPSCs into cholangiocytes to a functional significance that could enable multiple downstream applications such as developmental studies, accurate disease modeling and drug screening.

These advances were achieved through the development of a culture system reproducing key stages of natural bile duct development (FIG. 1). Importantly, our method enables for the first time the differentiation of hepatoblasts to a highly homogeneous population of early cholangiocyte progenitors (75% CK19+/Sox9+ cells) under chemically defined conditions. This differentiation stage constitutes a unique feature of our protocol compared to previous studies, providing an optimal starting population for the generation of mature CLC organoids and explaining in part the distinctive efficiency of our culture system. Furthermore, the generation of CLC organoids in vitro, resembles the process of tubulogenesis occurring during native bile duct development, which is regulated by Notch signaling. Indeed, the role of the JAG-Notch pathway for tubulogenesis is well described (1 11, 22, 41-45), while defects in Notch activity associated with AGS result in bile duct paucity (19). Nevertheless, the importance of Notch for organoid formation in vitro has not yet been demonstrated, as previous methods preclude such analyses. Therefore, our observations on the requirement for Notch signaling could allow developmental studies shedding light on the regulation of this pathway during biliary tree development and AGS. However, we note that our system cannot model the complex interactions between the different cell types constituting the liver neither fully mimic the niche where cholangiocytes develop and mature. Consequently, further work is required to validate these findings both in vivo and in vitro using AGS-derived hIPSCs.

The functional properties of our cells compared to previous protocols render our system an optimal platform for modeling biliary disorders caused by disruption of these key functions. Accordingly, based on the activity of CFTR in CLCs, the capacity of our platform to model cholangiopathies was demonstrated using hIPSCs from patients with CF liver disease (CF-hIPSCs). Using CF-CLC organoids, we were able to identify a new potential treatment for CF associated cholangiopathy, by demonstrating that the experimental compound VX809 can rescue the disease phenotype in vitro. Interestingly, although VX809 has been reported to correct CFTR processing defects (38), its effects in the context of cholangiocytes and CF Liver Disease (CFLD) have not been described before. Our findings are of particular importance given the fact that VX809 has already completed phase IIa clinical trials (39) and therefore could potentially be used in clinical trials in the context of liver disease with minimal delays. Overall, these results demonstrate the application of our platform for modeling CFLD in vitro, and illustrate the capacity of the resulting model for identifying novel therapeutic compounds for CFLD.

The potential of our culture system for testing and developing therapeutic agents in the context of cholangiopathies was further demonstrated by reproducing the effects of 2 compounds: verapamil and octreotide. In combination with the unique capacity of our platform for generating large quantities of near homogeneous populations of functional human CLCs, our method opens the possibility for high-throughput applications such as drug screening.

Considered collectively, these findings provide proof-of-principle for the suitability of cholangiocyte-like cells for drug validation, which becomes particularly important in light of the limitations of alternative platforms for pharmaceutical testing.

In conclusion, our culture system represents an enhanced and powerful tool that will advance research in the field of cholangiopathies by providing large numbers of autologous, disease specific biliary tissue for in vitro disease modeling, developmental studies, drug screening and target validation. More importantly, hIPSC derived cholangiocytes may complement recent advances on tissue engineering and possibly contribute to the generation of three-dimensional liver organoids incorporating a biliary system, thereby bringing us one step closer to the ultimate goal of regenerative medicine; the generation of personalized organs for the treatment of end stage disease.

REFERENCES

1. Lazaridis K N et al. *Gastroenterology* 127:1565-77 (2004).
2. Murray K F et al *Hepatology* 41:1407-32 (2005).
3. Pollheimer M J et al. *Clin Res Hepatol Gastro.* 35:792-804 (2011).
4. Takahashi K et al. *Cell,* 126:663-76 (2006).
5. Robinton D A et al. *Nature.* 481:295-305 (2012)
6. Dianat N et al. *Hepatology*, doi:10.1002/hep.27165 (2014).
7. Zhao D et al. *PLoS One,* 4(7):e6468 (2009).
8. Tanimizu N et al. *Mol Biol Cell.,* 18:1472-9 (2007).
9. Rashid S T et al. *J Clin Invest.* 120:3127-36 (2010).
10. Hannan N R et al. *Nat Protoc.* 8:430-7 (2013).
11. Si-Tayeb K et al. *Dev Cell.* 18:175-89 (2010).
12. Xia X et al. *World J Gastroenterol.* 12:3553-63 (2006).
13. Kanno N et al. *Hepatology* 31:555-61 (2000).
14. Minagawa N et al. *World J Gastroenterol.* 12:3466-70 (2006).
15. Gigliozzi A et al. *Gastroenterology,* 119:1113-22 (2000).
16. Cizková D et al. *Physiol Res.,* 54:419-28 (2005).
17. Antoniou A et al. *Gastroenterology,* 136:2325-33 (2009)
18. Clotman F et al. *Genes Dev.,* 19:1849-54 (2005).
19. Turnpenny P D et al. *Eur J Hum Genet.* 20:251-7 (2012).
20. Bray S J *Nat Rev Mol Cell Biol.,* 7:678-89 (2006).
21. Saravanamuthu S S et al. *Dev Biol.* 2009; 332:166-76.
22. Zong Y et al. *Development,* 136:1727-39 (2009).
23. Raynaud P et al. *Hepatology,* 53:1959-66 (2011).
24. Chandok N *Ann Hepatol.,* 11:819-26 (2012).
25. Temmerman F et al. *Aliment Pharmacol Ther.,* 34:702-13 (2011).
26. Caroli A et al. *Clin J Am Soc Nephrol.* 5:783-9 (2010).
27. Marinelli R A et al. *Am J Physiol.* 276:G280-6 (1999).
28. Gong A Y et al. *Am J Physiol Cell Physiol.,* 284:C1205-14 (2003).
29. Capema T J et al. *In Vitro Cell Dev Biol Anim.,* 47:218-33 (2011).
30. Masyuk T V et al. *Gastroenterology,* 132:1104-16 (2007).
31. Rowe S M et al. *N Engl J Med.,* 352:1992-2001 (2005).
32. Davies J C et al. *BMJ,* 335:1255-9 (2007).
33. Colombo C. *Curr Opin Pulm Med.,* 13:529-36 (2007).
34. Staufer K et al. *Int J Mol Sci.* 15:13529-49 (2007).
35. Ward C L et al. *J Biol Chem.* 269:25710-8 (1994)
36. Shenoy A et al. *Pediatr Res.* 2011; 70:447-52.
37. Haack A et al. *World J Gastroenterol.* 19:8552-8561 (2013).
38. Van Goor F et al. *Proc Natl Acad Sci USA.* 108:18843-8 (2011).
39. Clancy J P et al *Thorax,* 67:12-8 (2012).
40. Yanai M et al. *Dev Dyn.* 5 237:1268-83 (2008).
41. Kodama Y et al. *Gastroenterology.* 2004; 127(6):1775-86.

42. Tanimizu N et al. *J Cell Sci,* 117:3165-74 (2004).
43. Zong Y *Int J Biochem Cell Biol.,* 43:257-64 (2011).
44. Lemaigre F P *Hepatology,* 48:358-60 (2008).
45. Hofmann J J et al. *Development,* 137:4061-72 (2010).
46. Hannan N R et al. *Stem Cell Reports,* 1:293-306 (2013).
47. Du P et al. *Bioinformatics,* 24:1547-1548 (2008).
48. Smyth G K. *Stat. Appl. Genet. Mol. Biol.* 3: Article3 (2004).
49. Benjamini Y et al. *J. R. Stat. Soc.* 57:289-300 (1995).
50. Ramsay J O, Silverman B W. Functional Data Analysis, 2nd ed. Springer, New York, USA, 2006.

TABLE 1

|  | CLCs | hESC-Chol |
|---|---|---|
| Global gene expression profile compared to CBD | | |
| Spearman Rank correlation (Probes) | $p_{CLC} = 0.86$ | $p_{hESC-Chol} = 0.51$ |
| Spearman Rank correlation (Genes) | $p'_{CLC} = 0.83$ | $p'_{hESC-Chol} = 0.62$ |
| Mutual Information (MI) (Probes) | $MI_{CLC} = 0.62$ | $MI_{hESC-Chol} = 0.54$ |
| Mutual Information (MI) (Genes) | $MI'_{CLC} = 0.80$ | $MI'_{hESC-Chol} = 0.73$ |
| Expression of binary markers | See table S4 | See table S4 |
| Protocol | | |
| Chemically defined | Up to and including CPs | Based on serum |
| Cell expansion | 57 fold | Data not available |
| Efficiency | 75% | 31% |
| Functionality | | |
| MDR1 functionality | Present | Present |
| Bile acid transfer | Present | Paradoxical |
| ATP response | 95% | 70% |
| Acetylcholine response | 96% | 40% |
| VEGF response | Present | Not demonstrated |
| GGT activity | 1.6 X human serum | Not demonstrated |
| ALP activity | Present | Not demonstrated |
| Secretin response | 96% | Not demonstrated |
| Somatostatin response | 94% | 31% |
| CFTR activity | Present | Not demonstrated |
| Applications | | |
| Disease modeling | AGS, PLD, CF | Not demonstrated |
| Pharmacological agents tested | Octreotide, VX809 | None |

TABLE 3

| COMPONENT | g/L |
|---|---|
| INORGANIC SALTS | |
| $Ca(NO_3)_2 \cdot 4H_2O$ | 0.1 |
| MgSO4 (anhyd) | 0.04884 |
| KCl | 0.4 |
| NaHCO3 | 2.0 |
| NaCl | 6.0 |
| Na2HPO4 (Anhyd) | 0.8 |
| AMINO ACIDS | |
| L-Arginine (free base) | 0.2 |
| L-Asparagine (anhyd) | 0.05 |
| L-Aspartic Acid | 0.02 |
| L-Cystine•2HCl | 0.0652 |
| L-Glutamic Acid | 0.02 |
| L-Glutamine | 0.3 |
| Glycine | 0.01 |
| L-Histidine (free base) | 0.015 |
| Hydroxy-L-Proline | 0.02 |
| L-Isoleucine | 0.05 |
| L-Leucine | 0.05 |
| L-Lysine•HCl | 0.04 |
| L-Methionine | 0.015 |
| L-Phenylalanine | 0.015 |
| L-Proline | 0.02    0.02 |
| L-Serine | 0.03    0.03 |
| L-Threonine | 0.02    0.02 |
| L-Tryptophan | 0.005    0.005 |
| L-Tyrosine•2Na•2H2O | 0.02883    0.02883 |
| L-Valine | 0.02    0.02 |
| VITAMINS | |
| D-Biotin | 0.0002    0.0002 |
| Choline Chloride | 0.003    0.003 |
| Folic Acid | 0.001    0.001 |
| myo-Inositol | 0.035    0.035 |
| Niacinamide | 0.001    0.001 |
| p-Amino Benzoic Acid | 0.001    0.001 |
| D-Pantothenic Acid•½Ca | 0.00025    0.00025 |
| Pyridoxine•HCl | 0.001    0.001 |
| Riboflavin | 0.0002    0.0002 |
| Thiamine•HCl | 0.001    0.001 |
| Vitamin B-12 | 0.000005    0.000005 |
| OTHER | |
| D-Glucose | 2.0    2.0 |
| Glutathione (reduced) | 0.001    0.001 |

TABLE 2

| GENE | CLCs 1 | CLCs 2 | CLCs 3 | hESC-Chol 1 | hESC-Chol 2 | hESC-Chol 3 | hESC-Chol 4 | hESC-Chol 5 |
|---|---|---|---|---|---|---|---|---|
| SOX9 | 1254 | 1352 | 1198 | 5336 | 5491 | 5329 | 5614 | 5223 |
| HNF1B | 7848 | 7842 | 7943 | 10608 | 10382 | 10511 | 10468 | 10721 |
| ONECUT2 | 2490 | 2716 | 2653 | 11401 | 11420 | 11658 | 11697 | 11548 |
| SCTR | 8677 | 9197 | 8041 | 13393 | 13179 | | 13987 | 11780 |
| SSTR2 | 984 | 915 | 1039 | 11916 | 11843 | | 11627 | 11736 |
| CFTR | 8697 | 8295 | 8395 | 8877 | 9152 | | 9018 | 8978 |
| GGT1 | 7800 | 7861 | 7667 | 8546 | 8833 | | 8845 | 8642 |
| ALPL | 6811 | 6684 | 6652 | 11130 | 11152 | | 11162 | 11598 |
| HES1 | 2550 | 2520 | 2548 | 8107 | 8414 | | 8416 | 8124 |
| NOTCH1 | 1310 | 1381 | 1315 | 9387 | 8707 | | 8988 | 9211 |
| SLC9A2 | 9333 | 8114 | 8323 | 14190 | 14343 | | 14382 | 14236 |
| SLC9A4 | 9103 | 9188 | 8881 | 14724 | 14926 | | 15251 | 14517 |
| SLC10A2 | 12299 | 12170 | 14153 | 15690 | 14760 | | 15632 | 15808 |
| SLC51A | 5516 | 5523 | 5564 | 14344 | 15195 | | 15132 | 12552 |
| SLC26A2 | 2903 | 2862 | 2949 | 3713 | 3851 | | 3967 | 3638 |
| SLC4A8 | 10133 | 10616 | 10177 | 10941 | 10921 | | 10945 | 11017 |
| SLC4A4 | 4326 | 4397 | 4355 | 8924 | 8873 | | 8816 | 8595 |
| SLC12A2 | 1476 | 1294 | 1340 | 6885 | 7096 | | 7092 | 6685 |
| SLC10A7 | 9073 | 8597 | 9176 | 11022 | 11175 | | 10991 | 11009 |
| PPARG | 2524 | 2730 | 2571 | 6548 | 6595 | | 6585 | 6496 |
| PKD2 | 3105 | 3113 | 3221 | 5132 | 5303 | | 5279 | 5670 |

TABLE 3-continued

| COMPONENT | g/L | |
|---|---|---|
| HEPES | — | — |
| Phenol Red•Na ADD | 0.0053 | 0.0053 |
| NaHCO$_3$ | 2.0 | — |

The invention claimed is:

1. A method for producing a population of cholangiocyte progenitors (CPs) comprising:
   (i) culturing a population of foregut stem cells (FSCs) in a hepatic induction medium comprising bone morphogenetic protein (BMP) and a TGFβ signalling inhibitor to produce a population of hepatoblasts, and
   (ii) culturing the population of hepatoblasts in a biliary induction medium comprising fibroblast growth factor (FGF), retinoic acid and a TGFβ ligand to produce a population of cholangiocyte progenitors (CPs), wherein the TGFβ signalling inhibitor is a compound selected from the group consisting of SB-431542, SB-505124, lefty, cerberus and follistatin; and the TGFβ ligand is a compound selected from the group consisting of Activin, TGFP, Nodal, and GDF3.

2. A method according to claim 1 wherein the hepatic induction medium is a chemically defined nutrient medium which consists of a basal medium supplemented with bone morphogenetic protein (BMP) and a TGFβ signalling inhibitor; wherein the TGFβ signalling inhibitor is a compound selected from the group consisting of SB431542, SB-505124, lefty, cerberus and follistatin.

3. A method according to claim 1 wherein the TGFβ signalling inhibitor is SB-431542.

4. A method according to claim 1 wherein the biliary induction medium consists of a chemically defined nutrient medium supplemented with fibroblast growth factor (FGF), retinoic acid and a TGFβ ligand, wherein the TGFα ligand is a compound selected from the group consisting of Activin, TGFβ, Nodal, and GDF3.

5. A method according to claim 1 wherein the TGFp ligand is Activin.

6. A method according to claim 1 comprising:
   (iii) culturing the CPs in a cholangiocyte maturation medium comprising epidermal growth factor to produce a population of cholangiocyte-like cells (CLCs).

7. A method according to claim 6 wherein the CPs are cultured in the cholangiocyte maturation medium in three-dimensional culture.

8. A method according to claim 6 wherein the cholangiocyte maturation medium consists of a scaffold matrix and a chemically defined nutrient medium supplemented with EGF.

9. A method according to claim 6 wherein the CLCs form one or more organoids in the cholangiocyte maturation medium.

10. A method according to claim 6 wherein the CLCs express CK7, CK18, CK19, HNF1B, Gamma Glutamyl-Transferase (GGT), Jagged 1 (JAG1), NOTCH2, CFTR, SCR, SSTR2, Apical Salt and Bile Transporter (ASBT), Aquaporin 1 and Anion Exchanger 2.

11. A method according to claim 1 wherein the population of FSCs is produced by a method comprising;
   (a) culturing a population of pluripotent stem cells (PSCs) in an endoderm induction medium comprising a TGFβ ligand, fibroblast growth factor (FGF), Wnt signalling activator, bone morphogenetic protein (BMP) and a PI3K inhibitor to produce a population of definitive endoderm cells (DECs); wherein the TGFβ ligand is a compound selected from the group consisting of Activin, TGFβ, Nodal, and GDF3,
   (b) culturing the DECs in a foregut induction medium comprising a TGFβ ligand to produce a population of foregut stem cells (FSCs).

12. A method according to claim 11 wherein the endoderm induction medium consists of a chemically defined nutrient medium supplemented with a TGFβ ligand, fibroblast growth factor (FGF), GSK-β inhibitor, bone morphogenetic protein (BMP) and a PI3K inhibitor; wherein the TGFβ ligand is a compound selected from the group consisting of Activin, TGFα, Nodal, and GDF3.

13. A method according to claim 12 wherein the TGFp ligand is Activin, the GSK-3P inhibitor is CHIR99021 and/or the PI3K inhibitor is LY294002.

14. A method according to claim 1 comprising expanding, culturing, maintaining, or storing the population of CPs.

15. A method according to claim 1 comprising admixing the population of CPs with a therapeutically acceptable excipient.

16. A method according to claim 6 comprising expanding, culturing, maintaining, or storing the population of CLCs.

17. A method according to claim 6 comprising admixing the population of CLCs with a therapeutically acceptable excipient.

* * * * *